United States Patent [19]

Thornton et al.

[11] Patent Number: 5,143,726
[45] Date of Patent: * Sep. 1, 1992

[54] T CELL EPITOPES OF THE HEPATITIS B VIRUS NUCLEOCAPSID PROTEIN

[75] Inventors: George B. Thornton; Ann M. Moriarty; David R. Milich; Alan McLachlan, all of San Diego, Calif.

[73] Assignee: The Scripps Research Institute, La Jolla, Calif.

[*] Notice: The portion of the term of this patent subsequent to Apr. 4, 2006 has been disclaimed.

[21] Appl. No.: 439,099

[22] Filed: Nov. 20, 1989

Related U.S. Application Data

[63] Continuation of Ser. No. 106,538, Oct. 7, 1987, Pat. No. 4,882,145, which is a continuation-in-part of Ser. No. 939,617, Dec. 9, 1986, Pat. No. 4,818,527.

[51] Int. Cl.$^5$ .................... A61K 39/00; A61K 39/29; C07K 7/00; C07K 15/00
[52] U.S. Cl. ........................................ 424/88; 424/89; 530/324; 530/325; 530/326; 530/327; 530/328; 530/345; 530/350; 530/403; 530/806; 530/809; 530/826

[58] Field of Search ............... 530/324, 325, 345, 326, 530/327, 350, 328, 806, 807, 826; 424/88, 89

[56] References Cited

U.S. PATENT DOCUMENTS 4,818,527  4/1989  Thornton et al. ............... 424/88
4,882,145  11/1989  Thornton et al. ............... 424/88

OTHER PUBLICATIONS

Clark et al., Nature, 330:381-384 (1987).
Rudinger, Peptide Hormones, Parsons (Ed.) U. Park Press, Baltimore, pp. 1-7 (1976).
Talmadge et al., 13th International Congress of Chemotherapy, Proceedings (Spitzy et al. Ed.) pp. 203/19-203/35 (1983).

Primary Examiner—Y. Christina Chan
Attorney, Agent, or Firm—Douglas A. Bingham

[57] ABSTRACT

Polypeptides corresponding in amino acid residue sequence to T cell stimulating regions of the HBV nucleocapsid protein are disclosed. A method of enhancing the immunogenicity of a polypeptide immunogen comprising operatively linking the polypeptide through an amino acid residue side chain to core protein particles is also disclosed.

5 Claims, 20 Drawing Sheets

PRE-S POLYPEPTIDE

```
              1         2         3         4         5         6
     12345678901234567890123456789012345678901234567890123456789012
1 ayw  GHHILGNKIYSMGQNLSTSNPLGFFPDHQLDPAFRANTANPDWDFNPNKDTWPDANKVGAGA
2 adyw GHHILGNKSYSMGQNLSTSNPLGFFPDHQLDPAFRANTNNPDWDFNPNKDTWPDANKVGAGA
3 adw2 MGGWSSKPRKGMGTNLSVPNPLGFFPDHQLDPAFGANSNNPDWDFNPVKDDWPAANQVGVGA
4 adw  LGHKSTSIRKGMGTNLSVPNPLGFLPDHQLDPAFGANSTNPDWDFNPIKDHWPAANQVGVGA
5 adr4 MGGWSSKPRQGMGTNLSVPNPLGFFPDHQLDPAFGANSHNPDWDFNPNKDHWPEANQVGAGA
6 adr  MGGWSSKPRQGMGTNLSVPNPLGFFPDHQLDPAFGANSNNPDWDFNPNKDQWPEANQVGAGA
            MG  NLS  NPLGF PHDQLDPAF AN  NPDWDFNP KD WP AN VG GA
            ..  ...  ..... ......... ..  ........ .. .. .. .. ..

6         7         8         9        10        11        12
     345678901234567890123456789012345678901234567890123456789012345
1 ayw  FGLGFTPPHGGLLGWSPQAQGILQTLPANPPPASTNROSGRQPTPLSPPLRNTHPQAMQWNS
2 adyw FGLGFTPPHGGLLGWSPQAQGIMQTLPANPPPASTNRQSGRQPTPLSPPLRTTHPQAMHWNS
3 adw2 FGPRLTPPHGGILGWSPQAQGILTTVSTIPPPASTNRQSGRQPTPISPPLRDSHPQAMQWNS
4 adw  FGPGLTPPHGGILGWSPQAQGILTTVSTIPPPASTNRQSGRQPTPISPPLRDSHPQAMQWNS
5 adr4 FGPGFTPPHGGLLGWSPQAQGVLTTVPVAPPPASTNRQSGRQPTPISPPLRDSHPQAMQWNS
6 adr  FGPGFTPPHGGLLGWSPQAQGILTTVPAAPPPASTNRQSGRQPTPISPPLRDSHPQAMQWNS
       FF  TPPHGG LGWSPQAQG  T   PPPASTNRQSGRQPTP SPPLR  HPQAM WNS
       ..  ...... .........  .   ................ .....  ..... ...

12        13        14        15        16        17
     567890123456789012345678901234567890123456789012345678901234
1 ayw  TTFHQTLQDPRVRGLYFPAGGSSSGTVNPVLTTASPLSSIFSRIGDPALN
2 adyw TTFHQTLQDPRVRGLYFPAGGSSSGTVNPVPTTTSPISSIFSRIGDPALN
3 adw2 TAFHQTLQDPRVRGLYLPAGGSSSGTVNPAPNIASHISSISARTGDPVTN
4 adw  TALHQALQDPRVRGLYLPAGGSSSGTVNPAPNIASHISSISARTGDPVTI
5 adr4 TTFHQALLDPRVRGLYFPAGGSSSGTVNPVPTTASPISSISSRTGDPAPN
6 adr  TTFHQALLDPRVRGLYFPAGGSSSGTVNPVPTTASPISSIFSRTGDPAPN
         T  HQ L DPRVRGLY PAGGSSSGTVNP     S  SSI  R GDP
         .  .. . .......... ............     .  ...  . ....
```

FIG.2

MENITSGFLGPLLVLQAGFFLLTRILTIPQSLDSWWTSLNFLGGTTVCLGQNSQSPTSNHSPTSCPPTCPGYRWMCLRRF

IIFLFILLLCLIFLLVLLDYQGMLPVCPLEPGSSTTSTGPCRTCMTTAQGTSMYPSCCCTKPSDGNCTCIPIPSSWAFGK

FLWEWASARFSWLSLLVPFVQWFVGLSPTVWLSVIWMMWYWGPSLYSILSPFLPLLPIFFCLWYI

FIG.3

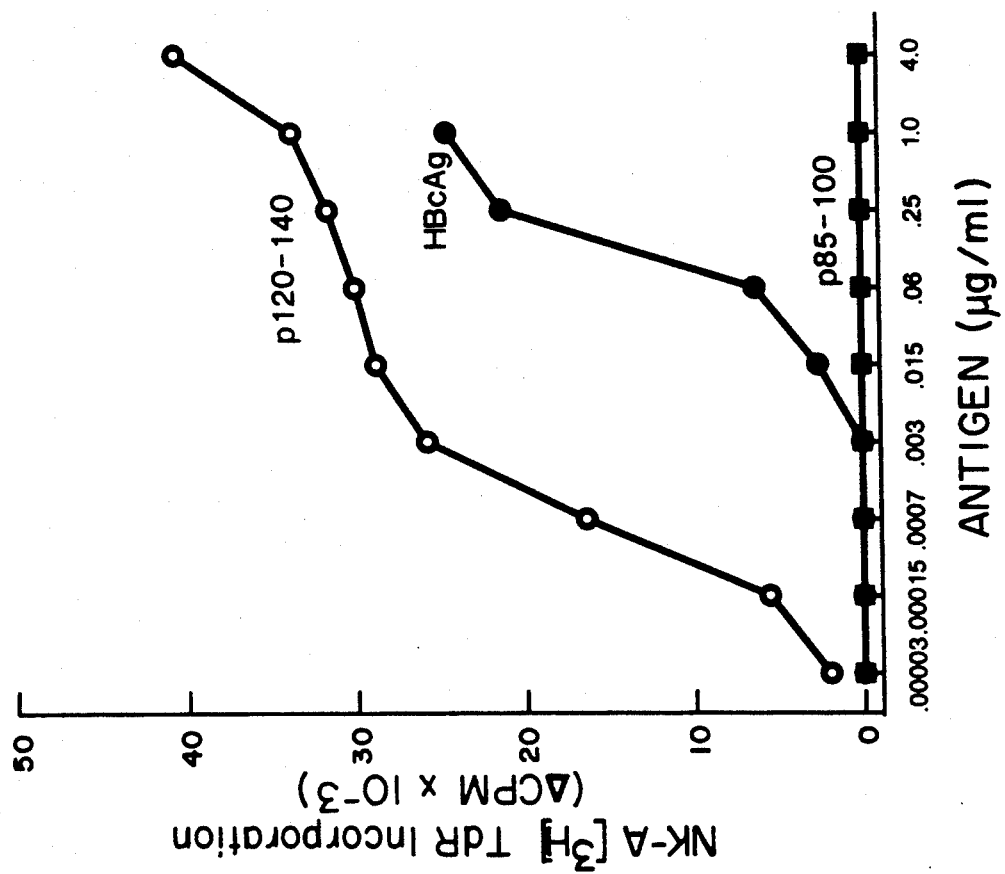
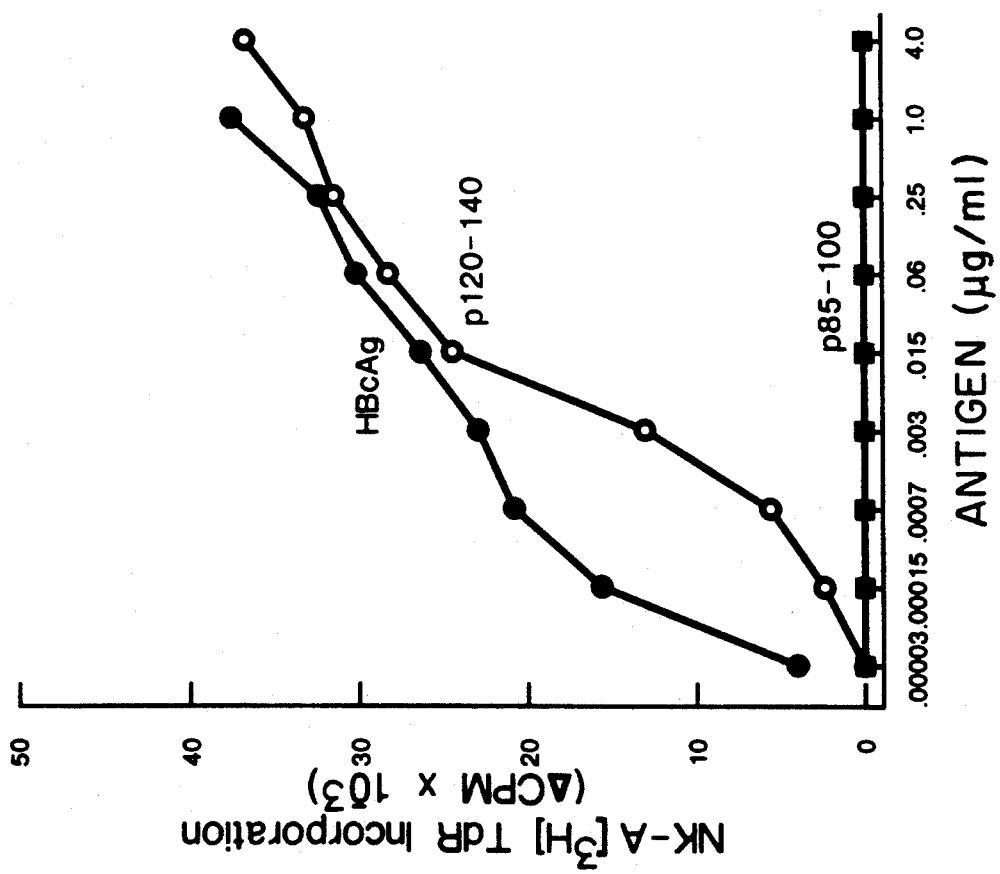

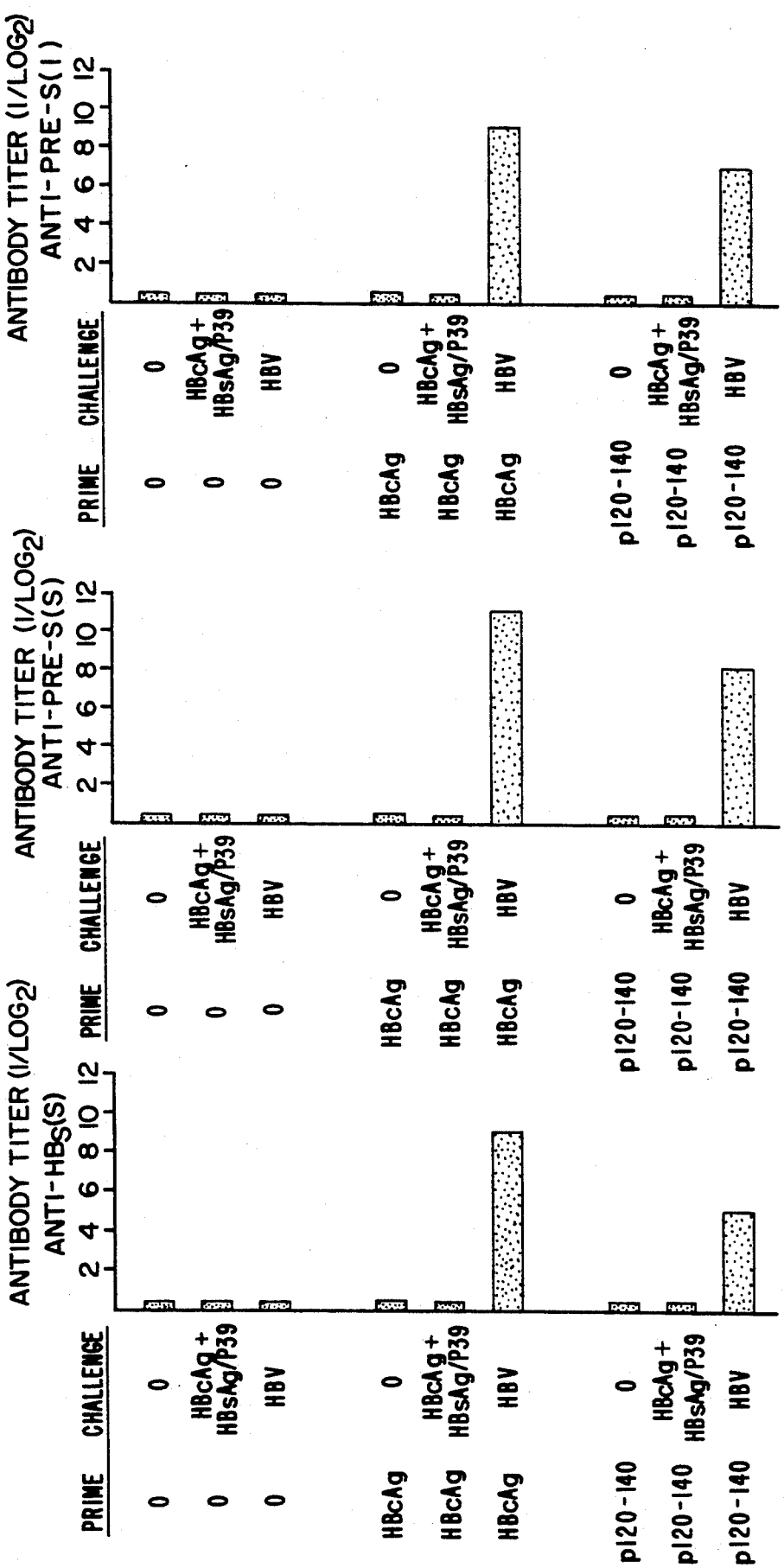

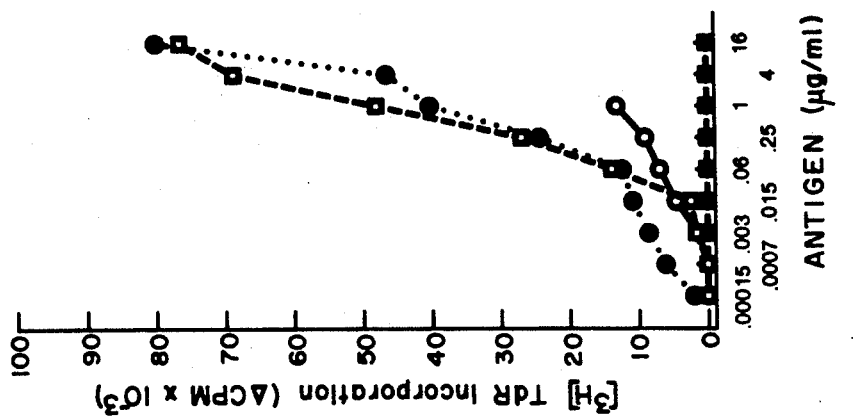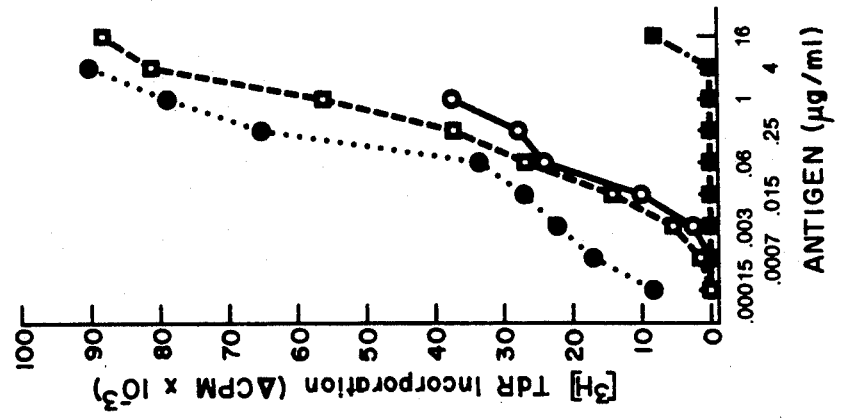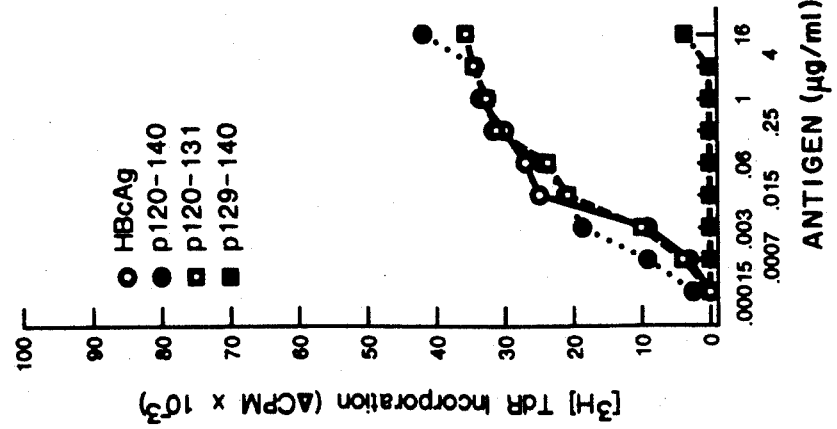

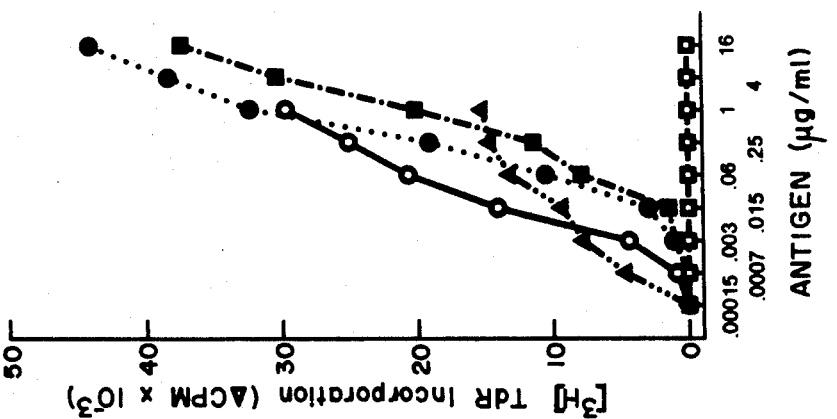
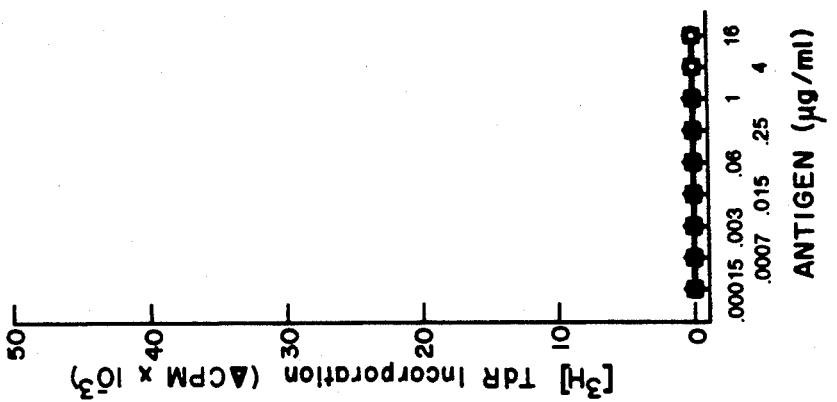
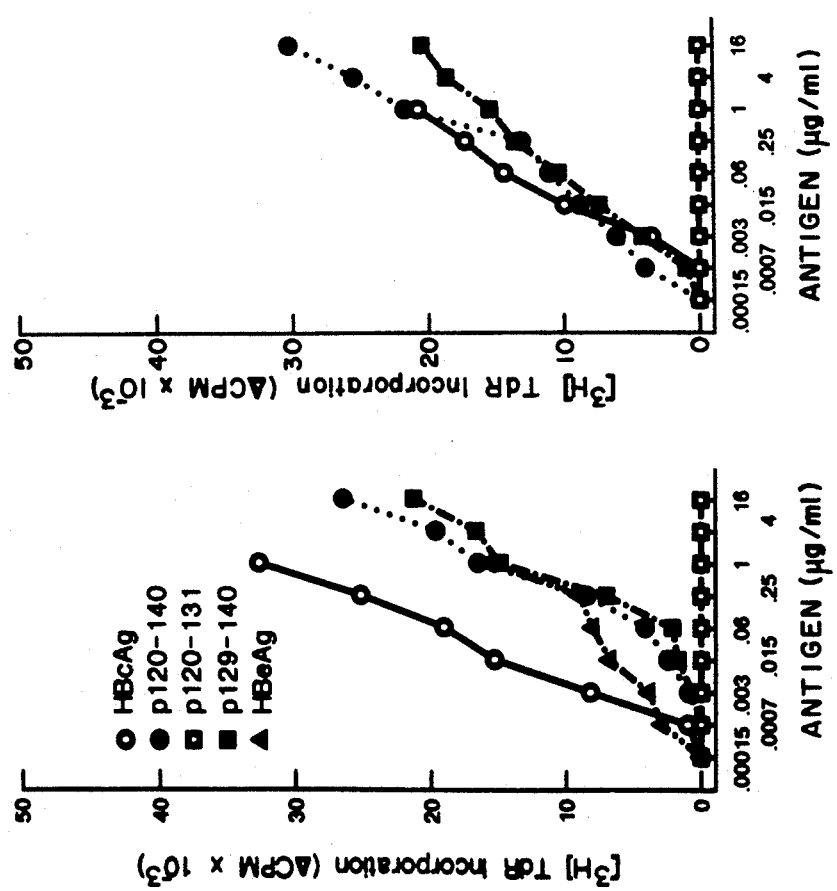

T CELL EPITOPES OF THE HEPATITIS B VIRUS NUCLEOCAPSID PROTEIN

CROSS-REFERENCE TO RELATED APPLICATION

This application is a continuation application of the application having the Ser. No. 07/106,538, filed Oct. 7, 1987 that has issued as U.S. Pat. No. 4,882,145 on Nov. 21, 1989 which is itself a continuation-in-part of application Ser. No. 939,617, filed Dec. 9, 1986, that has issued as U.S. Pat. No. 4,818,527 on Apr. 4, 1989.

TECHNICAL FIELD OF THE INVENTION

The present invention relates to the production of novel synthetic antigens related to the hepatitis B virus nucleocapsid protein (HBcAg) and to the use of those antigens in the production of vaccines, therapeutic agents and the like. More specifically, this invention relates to polypeptide compositions that contain HBcAg T cell determinants.

BACKGROUND OF THE INVENTION

In his classic work *The Specificity of Serological Reactions* published in 1936, Landsteiner showed that antibody formation against a simple azo compound could be induced by coupling the compound to an immunogenic molecule such as serum protein. Although the simple azo molecule would not elicit antibody formation when injected alone, the azo-protein conjugate elicited the production of anti-azo antibodies as well as anti-protein antibodies when injected into animals. The notion that the small nonimmunogenic molecule was using the large immunogenic protein molecule as a carrier was thus developed. The molecule which derived immunogenicity by being conjugated to the carrier was termed the hapten.

The phenomenon of a relatively large molecule potentiating the immunogenicity of a small molecular entity to which it is attached is known in the art as the "carrier effect".

Carrier effects can be defined as immunity to one determinant (the 'helper' or T cell determinant) of a multideterminant immunogen enhancing the response to another determinant (the B cell determinant). Thus, T cells, by recognizing helper determinants on the antigen somehow help B cells to make antibody against the B cell specific antigen. Furthermore, it is now known that carrier effects are not confined to hapten-protein conjugates and can be demonstrated, for example, with subunits on protein molecules. Rajewsky et al., *J. Exp. Med.* 126:581 (1967).

It is now well established that most antigens require T-cell help to induce B cells to produce antibodies. Classic cognate T cell help requires direct T cell-B cell interaction mediated by an antigen bridge. According to Rajewsky et al., *J. Exp. Med.*, 129:1131 (1969), the antigenic determinants recognized by T helper cell (Th) and B cells must be covalently linked to form a single molecular entity. More recently, several groups have suggested that covalent linkage may not be necessary when the T cell determinant and B cell determinant are presented in the context of a large particle, such as a virus. This mechanism of T cell help has been termed intermolecular/intrastructural because the T and B cell determinants are present on molecular entities that are not covalently linked but are operatively linked in terms of T and B cell interaction because they are within a structure the immune system sees as being unitary. See, Russel et al., *Nature*, 280:147 (1979), Lamb et al., *J. Immunol.*, 129:1465 (1982), Scherle et al., *J. Exp. Med.*, 164:1114 (1986), and Lake et al., *Cold Spring Harbor Symp. Quant. Biol.*, 41:589 (1976). Some, however, can induce antibody formation in the absence of T-cells. These are called thymus-independent (T-independent) antigens. Most, if not all, antigens which act in the absence of helper T-cells are composed of repeating subunits of the same antigenic determinant. The most commonly used T-independent antigens are polymerized flagellin (a protein of repeating subunits) or various polysaccharides (which are repeating units of sugars).

Hapten-carrier conjugates are widely used today in determining the function of the various cells in the immune response. However, while hapten-carrier conjugates have served the research community well in its investigations of the nature of the immune response, they have not yet been of significant use in the production of immunogens that play a role in diagnostic or therapeutic modalities.

Recently, it has been determined that a pathogen related protein can be immunologically mimicked by the production of a synthetic polypeptide whose sequence corresponds to that of a determinant domain of the pathogen related protein. Such findings are reported by Sutcliffe et al., *Nature*, 287:801 (1980), and Lerner et al., *Proc. Natl. Acad. Sci. USA*, 78:3403 (1981).

Moreover, Gerin et al., (1983) *Proc. Natl. Acad. Sci. USA*, 80:2365 have recently shown limited protection of chimpanzees from hepatitis B virus upon immunization with carrier-bound synthetic polypeptides having amino acid residue sequences that correspond to the sequence of a determinant portion of HBsAg; in particular, residues 110–137 of the "S" (surface) region. However, the carrier protein used in these studies was keyhole limpet hemocyanon (KLH), a T cell dependent carrier that is not fit for use in humans because it is a source of irritation that leads to severe inflammation.

The art has long sought a T cell stimulating carrier protein capable of enhancing the immunogenicity of polypeptide immunogens that does not produce unacceptable side effects in human subjects. Immunogenic natural proteins, particularly tetanus toxoid, have been used most frequently when a carrier suitable for human administration was needed. However, even the use of tetanus toxoid as a carrier has been restricted due to problems with dosage limitations and risk of sensitization to the toxoid itself. In addition, an epitopic specific suppression can occur even in individuals already immunized against tetanus.

Vigorous efforts in pursuit of identifying highly immunogenic carrier proteins have resulted in Delpeyroux et al., *Science*, 233:472–475 (1986) reporting the use of the HBV surface protein (S protein) as a carrier for a poliovirus polypeptide immunogen. Those investigators constructed a recombinant deoxyribonucleic acid (DNA) protein expression vehicle that produces a fusion protein, designated HBsPolioAg, capable of forming particles closely resembling authentic 22-nanometer HBsAg particles. HBsPolioAg consists of HBV S protein having an 11 amino acid residue sequence insert corresponding to amino acids 93–103 of capsid protein VPI of poliovirus type 1 (Mahaney strain).

Delpeyroux et al. reported that antisera from mice immunized with HBsPolioAg had a significant titer of poliovirus neutralizing antibodies. However, they also reported that the "best titer obtained was low by poliovirus standards and further work to improve the titer is needed".

BRIEF SUMMARY OF THE INVENTION

The present invention contemplates an immunogenic polypeptide conjugate that comprises a HBcAg protein operatively linked through an amino acid residue side chain to a polypeptide immunogen. In preferred embodiments the conjugate comprises, the particulate core protein operatively linked to a pathogen related immunogen such as HBsAg.

Also contemplated is an immunogenic fusion protein comprising HBcAg protein operatively linked at its carboxy-terminus by a peptide bond to a polypeptide immunogen, preferably a pathogen related immunogen and more preferably HBsAg. In addition, the fusion proteins of the present invention comprise HBcAg proteins operatively linked by a peptide bond to a pathogen related protein. Preferably, the amino acid residues of the polypeptide immunogen are substituted for a number of, preferably an identical number of, core protein amino acid residues.

Further contemplated is a T cell stimulating polypeptide consisting essentially of about 15 to about 70 amino acid residues having a sequence corresponding to a region of the HBV core protein from about amino acid residue position 70 to about position 140 from the amino terminus of the core protein.

Additionally contemplated is a composite polypeptide immunogen having at least 20 amino acid residues and including a T cell stimulating polypeptide consisting essentially of about 15 to about 70 amino acid residues having a sequence corresponding to the amino acid residue sequence of core protein from about position 70 to about position 140 from the amino terminus of the core protein. The T cell stimulating polypeptide is operatively linked to a polypeptide immunogen.

The present invention also contemplates a method of enhancing the immunogenicity of a polypeptide immunogen, preferably a pathogen related immunogen, that comprises operatively linking an HBcAg T cell epitope containing polypeptide to the immunogen.

BRIEF DESCRIPTION OF THE DRAWINGS

In the drawings, which constitute a portion of this disclosure:

FIG. 1 illustrates the amino acid residue sequence from left to right, in the direction from amino-terminus to carboxy-terminus and using single letter amino acid residue code, of the core protein of HBV subtype ayw. The sequences for other subtypes are well known in the art.

FIG. 2 illustrates the amino acid residue sequence, oriented as in FIG. 1 and using single letter amino acid residue code, of the pre-S region of HBsAg of six subtypes of HBV. The additional line of residues shown are those that are homologous in all six subtypes. The numerals above the sequences illustrate the sequence positions from the amino-terminus, with each tenth position numeral being represented vertically rather than in the usual horizontal manner. The sequences for the subtypes were reported as follows: ayw—Galibert et al., (1979) *Nature,* 281;646; adw/adr—Ono et al., (1983) *Nucl. Acids Res.,* 11:1747; $adw_2$—Valenzuela et al., (1908) in *ICN-UCLA Symposia on Animal Virus Genetics,* Fields et al., eds. pp 57–70, Academic Press; adyw—Pasek et al., (1979) *Nature,* 282:575; and $adr_4$—Fujiyama et al., (1983) *Nucl. Acids Res.,* 11:4601.

FIG. 3 illustrates the 226 amino acid sequence of the S from the HBV ayw subtype HBsAg/ayw protein, oriented as in FIG. 1 and using single letter amino acid residue code, as translated by Pasek et al., (1979) *Nature,* 282:575 from the nucleic acid sequence. Nucleotide sequence determinations of other HBV subtypes can be found in Pasek et al., Id.; Valenzuela et al., (1979) *Nature,* 280:815–819; and Galibert et al., (1979) *Nature,* 281:646–650.

FIG. 4 illustrates that particulate core protein can function as a T cell-independent antigen. Groups of five B10.BR euthymic (+/+) (Panel A) or B10.BR athymic (nu/nu) (B) mice were immunized intraperitoneally with a single dose of the 4.0 ug (●), 1.5 ug 0, or 0.5 ug (■) of particullate core protein in the form of *E, coli*-derived, recombinant BHcAg (rHBcAg; Biogen) or with 1.5 ug (□) of denatured core protein (D-HBcAg) in CFA. Particulate core was denatured by treatment with a final concentration of 0.1% SDS and 0.1% 2-mercaptoethanol for 2 hours at 37° C. At 10 and 24 days after immunization, sera were collected, pooled, and analyzed for anti-HBcAg antibodies activity by solid-phase RIA. Particulate core or D-HBcAg served as the solid-phase ligand, goat antibody to mouse Ig was the second antibody, and $^{125}$I-labelled swine antibody to goat Ig was used as the probe. Data are expressed as the reciprocal of the highest serum dilution to yield 4× the counts of preimmunization sera.

FIG. 5 illustrates that HBcAg efficiently stimulates T cells. Groups of 4 mice of the indicated strains were immunized with 4 ug of HBcAg in CFA in the hind footpads, and 8 days later draining lymph node cells were harvested and cultured in vitro with varying concentrations of HbcAg, particulate core protein. Supernatants were collected after 24 hours of culture and assayed for IL-2 production.

The high responding strains demonstrated HBcAg-specific, T cell activation at an HBcAg concentration as low as 0.03 ng/ml, which is equivalent to 0.0014 nM.

FIG. 6 illustrates the effect of immunization dose on the HBcAg-specific T cell proliferative response. Groups of 4 C3H.Q mice were immunized with either 12, 8, 4 or 1 ug of particulate core protein in CFA into the hind footpads, and 8 days later draining lymph node cells were cultured with varying concentrations of particulate, and after 96 hours of culture, T cell proliferation was determined by [$^3$H]-TdR incorporation.

FIG. 7 illustrates that the production of anti-HBcAg antibodies precedes and is of greater magnitude than that of anti-HBsAg in euthymic Balb/c mice. Groups of five Balb/c euthymic (+/+) (Panel A) or Balb/c athymic (nu/nu) (Panel B) mice were immunized intraperitoneally with a mixture of rHBcAg (8 ug) and HBsAg (8 ug) in CFA. Serum samples obtained before and 6, 12 and 24 days after immunization were pooled, and analyzed for anti-HBcAg and anti-HBsAg activity by RIA. Data are expressed as the reciprocal of the $\log_2$ of the highest serum dilution to yield 4× the counts of preimmunization sera.

FIG. 8 illustrates that HBcAg and HBeAg are cross-reactive at the T cell level. Groups of four $C_3$H.Q mice were primed in the hind footpads with either 4.0 ug of particulate core protein (Panel A) or 4.0 ug of denatured HBcAg (D-HBcAg) (Panel B) in CFA. After 8 days, draining lymph node cells were harvested, pooled, and cultured with varying concentrations of particulate core protein, sonicated HBcAg (D$_s$-HBsAg), at various concentrations ranging from 0.0015 to 1.0 micrograms per milliliter (ug/ml). In addition, some T cells primed with particullate core protein (Panel A) were cultured in the presence of various concentrations (0.06 to 240 ug/ml) of synthetic polypeptide p100-120. T cell activation was measured by antigen-induced, IL-2 production. IL-2 production is expressed as $^3$H-TdR incorporation by NK-A cells cultured in supernatant from antigen-treated cultures minus incorporation that occurred in supernatant from control cultures not treated with antigen (deltaCPM). This is a representiative assay of experiments performed on three separate occasions.

FIG. 9, Panels A through G, illustrate the localization of T cell sites within the HBcAg/HBeAg sequence using synthetic peptides. Groups of 4 mice each of the indicated strains were immunized with 4 ug of particulate core protein and draining lymph node cells were harvested 8 days post-immunization and cultured in vitro with the synthetic peptide fragments shown or particulate core protein as the positive control. T cell activation was measured by IL-2 production and the IL-2 production elicited by the optimal concentration of peptide (determined for each peptide and ranging from 25 to 64 ug/ml) is shown. The particulate core protein HBcAg concentration was 0.5 ug/ml.

Distinct peptides were recognized by the differing murine strains. The C$_3$H.Q strain recognized the p1-20 and the p100-120 sequences. The B10.S strain (Panel B) recognized the p28-52 and the p120-140 sequences. The B10.D2 stain (Panel C) recognized the p70-94, p85-100 (overlapping) and p120-140 sequences. The B10 strain recognized the p120-140 sequence exclusively. The B10.M strain recognized the p100-120 sequence exclusively. T cell recognition sites for the B10.BR and B10.P strains (Panels E and F, respectively) have not yet been identified. All the active sites are common to both the HBcAg and HBeAg sequences suggesting these antigens are crossreactive at the T cell level.

FIG. 10, Panels A and B, illustrate ability of synthetic peptide p120-140 to both induce and elicit an HBcAg - specific T cell proliferation response in the B10.S strain. Groups of 4 mice were immunized in the hind footpads with either 4 ug of particulate core protein (HBcAg, Panel A) or 100 ug of p120-140 (Panel B), and 8 days later draining lymph nodes were harvested and cultured with particullate core protein HBcAg, peptide p120-140 or peptide p85-100 in vitro at the various concentrations shown, and IL-2 production was determined.

HBcAg-primed B10.S strain T cells recognized p120-140 very efficiently. Inspection of the dose response curve demonstrates that a p120-140 concentration as low as 0.00015 ug/ml was sufficient to elicit IL-2 production. B10.S strain, HBcAg-primed T cells did not recognize the p85-100 sequence. In the reciprocal experiment B10.S mice were primed with p120-140 (Panel B). The p120-140-primed T cells recognized the immunizing peptide and not the p85-100 sequence, and recognized the native HBcAg.

FIG. 11, Panels A and B, illustrate the results of a study similar to that described in FIG. 10 but using the B10 mouse strain. Here the dose response curves for HBcAg (particulate core protein) and p120-140 appear to be even more closely related than in the B10.S strain (FIG. 10). This may indicate that p120-140 represents the only T cell recognition site relevant for the B10 strain.

FIG. 12, Panels A, B and C, illustrate the ability of peptide fragments p100-120 and p1-20 to both induce and elicit a HBcAg-specific T cell proliferative response in the C$_3$H.Q strain. This study was also performed in a manner similar to that shown in FIG. 10. C$_3$H.Q T cells were primed in vivo with either particullate core protein (HBcAg; Panel A) synthetic peptide p1-20 (Panel B) or syntheticc peptide p100-120 (Panel C). In vitro proliferative stimulus was provided by particcullate core protein (HBcAg), p100-120 or p1-20 at the various antigen concentrations shown.

FIG. 13, Panels A and B, illustrates the ability of peptide fragment p85-100 to both induce and elicit an HBcAg-specific T cell proliferative response in the B10.D2 strain. Again this study was performed in a manner similar to that shown in FIG. 10. B10.D2 T ccells were primed in vivo with either particulate core protein (HBcAg; Panel A) or peptide p85-100 (Panel B). In vitro proliferative stimulus was provided by particulate core protein (HBcAg) p85-100 or p120-140 at the various concentrations shown.

FIG. 14 illustrates HBcAg-primed and p120-140-primed Th cells of B10.S mice can induce antibody production specific for the S (FIG. 14A), pre-S(2) (FIG. 14B) and pre-S(1) regions of the envelope of HBV. B10.S mice were primed with either CFA alone (0,, upper panel), 4.0 ug of HBcAg in CFA (middle panel) or 100 ug of p120-140 in CFA (lower panel), and challenged three weeks later with a suboptimal dose of either a mixture (admixed but not operatively linked) of HBcAg and HBsAg/P39 (which possesses pre-S(1), pre-S(2) and S region antigens), or HBV in incomplete adjuvant or adjuvant alone. Sera were collected seven days after the challenge and analyzed for IgG antibody specific for the S, pre-S(2) and pre-S(1) regions of HBsAg by solid-phase RIA.

FIG. 15 illustrates a schematic representation of T helper cell-B cell interactions regulating the immune responses to the hepatitis B virus and subviral particles (spheres, filaments). The B cell (antibody) columns depict antigenic epitopes to which antibody is produced. The T cell columns depict specificities of Th cells which can provide functional help for antibody production to the various B cell determinants. All the Th-B cell interactions shown have been experimentally substantiated with the exception of the ability of S-specific Th cells to help anti-pre-S(2) and anti-pre-S(1) antibody production, and the ability of pre-S(2)-specific Th cells to help anti-pre-S(1) antibody production, which are inferred. The relative quantities of virions and subviral particles circulating in the serum, and the differential expression of the pre-S antigens on the various morphologic forms during and in the absence of viral replication are also depicted.

FIG. 16 illustrates the specificity of T cell recognition of HBcAg in the B10.S (H-2$^s$) strain. Groups of four B10.S mice were immunized in the hind footpads with either (a) 4.0 ug of HBcAg; (b) 100 ug of the synthetic peptides p120-140; (c) p120-131; or (d) p129-140 in CFA. Eight days after the priming, draining PLN cells were harvested, pooled, and cultured with the indicated concentrations (0.00015-16 ug/ml) of HBcAg, p120-140, p120-131, p129-140, or media alone, and T cell proliferation was measured by $^3$H-TdR incorporation. The data are expressed as CPM corrected for background proliferation in the absence of antigen (CPM). Background proliferation ranged from 800-2000 CPM.

FIG. 17 illustrates the specificity of T cell recognition of HBcAg in the B10 (H-2$^b$) strain. Groups of four B10 mice were immunized in the hind footpads with (a) 4.0 ug of HBcAg; (b) 100 ug of the synthetic peptides p120-140; (c) p120-131; or (d) p129-140 in CFA. Eight days after priming, draining PLN cells were harvested, pooled, and cultured with the indicated concentrations (0.00015-16 ug/ml) of HBcAg, HBeAg, p120-140, p120-131, p129-141, or media alone, and T cell proliferation was determined as described in FIG. 16.

FIG. 18 illustrates synthetic T cell sites of HBcAg represented by p120-140, p120-131, and p129-140 can prime Th cells which induce anti-HBc production in vivo. Groups of five B10.S (FIG. 18A) or B10 (FIG. 18B) mice were primed (1*) by i.p. immunization with 100 ug of either p120-140, p120-131, p129-140 in CFA or CFA alone. After three weeks, the primed mice were challenged (2*) with either a suboptimal dose of HBcAg (0.1 ug) in incomplete adjuvant or with adjuvant alone (0). Seven days after the challenge dose, sera were collected, pooled and analyzed for IgG class, anti-HBc antibody by solid-phase RIA. The anti-HBc titer is expressed as the highest serum dilution required to yield four times the counts of sera before immunization.

FIG. 19 illustrates the specificity of T cell recognition of the synthetic immunogen c120-140-(133-140) in the B10.S, B10, and B10.BR strains. Groups of 4 B10.S (FIG. 19A), B10 (FIG. 19B), or B10.BR (FIG. 19C) mice were immunized with 100 ug of c120-140-(133-140) in CFA into the hind footpads. Eight days after immunization, draining PLN cells were harvested, pooled, and cultured with varying concentrations of the indicated antigens, and the proliferative T cell responses were determined as described in FIG. 1. The level of T cell proliferation induced by 1.0 uq/ml concentration of the indicated antigens is depicted. Background proliferation ranged from 500-1500 CPM.

DETAILED DESCRIPTION OF THE INVENTION

A. Definitions

The term "antibody" refers to a molecule that is a member of a family of glycosylated proteins called immunoglobulins, which can specifically combine with an antigen.

The word "antigen" has been used historically to designate an entity that is bound by an antibody, and also to designate the entity that induces the production of the antibody. More current usage limits the meaning of antigen to that entity bound by an antibody, while the word "immunogen" is used for the entity that induces antibody production. Where an entity discussed herein is both immunogenic and antigenic, reference to it as either an immunogen or antigen will typically be made according to its intended utility.

"Antigenic determinant" refers to the actual structural portion of the antigen that is immunologically bound by an antibody combining site or T cell receptor. The term is also used interchangeably with "epitope".

The word "conjugate" as used herein refers to two or more polypeptides operatively linked through an amino acid residue side chain.

The term "conservative substitution" as used herein denotes that one amino acid residue has been replaced by another, biologically similar residue. Examples of conservative substitutions include the substitution of one hydrophobic residue such as isoleucine, valine, leucine or methionine for another, or the substitution of one polar residue for another such as between arginine and lysine, between glutamic and aspartic acids or between glutamine and asparagine and the like. The term "conservative substitution" also includes the use of a substituted amino acid in place of an unsubstituted parent amino acid provided that antibodies raised to such a polypeptide also immunoreact with the corresponding polypeptide having the unsubstituted amino acid.

The term "corresponds" in its various grammatical forms as used in relation to peptide sequences means the peptide sequence described plus or minus up to three amino acid residues at either or both of the amino- and carboxy-termini and containing only conservative substitutions in particular amino acid residues along the polypeptide sequence.

"Epitope" refers to that portion of a molecule that is specifically bound by a T cell antigen receptor or an antibody combining site.

As used herein, the term "fusion protein" designates at least two amino acid residue sequences not normally found linked together in nature operatively linked together end-to-end (head-to-tail) by a peptide bond between their respective terminal amino acid residues. The fusion proteins of the present invention are capable of inducing the production of antibodies that immunoreact with a polypeptide or pathogen-related immunogen that corresponds in amino acid residue sequence to the polypeptide or pathogen-related portion of the fusion protein.

Figure 1:
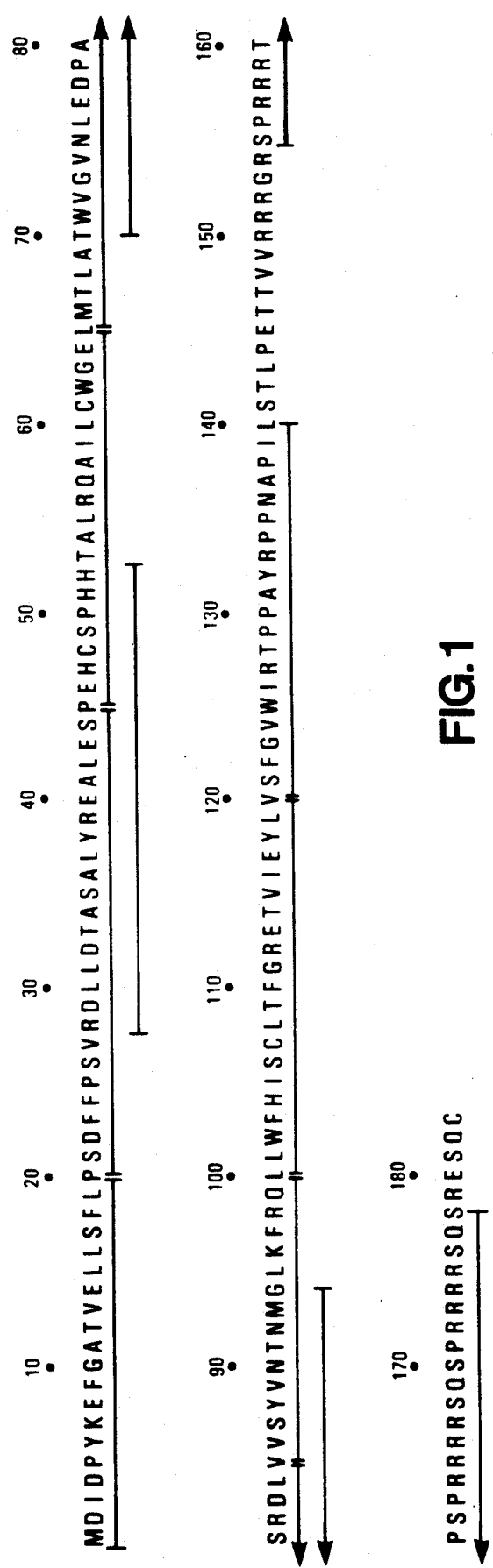

The phrase "HBcAg" as used here refers to T cell stimulating proteins or polypeptides having an amino acid residue sequence that corresponds to an amino acid residue sequence encoded by the hepatitus B virus nucleocapsid protein gene. Exemplary well known naturally occurring proteins encoded by the HBV nucleocapsid gene are the "core" protein, having an amino acid residue sequence as shown in FIG. 1, the precursor HBeAg protein that includes the sequence shown in FIG. 1, and the HBeAg protein that is a polypeptide portion of the sequence shown in FIG. 1. If reference is made to a polypeptide portion of any of the above described naturally occurring HBV nucleocapsid gene encoded proteins, that reference is explicit, either by stating, for example, that a T cell stimulating portion of the particular protein is referred to or by explicitly designating the particular portion of the sequence, as by indication of the included amino acid residue positions.

The term "immunoreact" in its various forms means binding between an antigen as a ligand and a molecule containing an antibody combining site such as a Fab portion of a whole antibody.

The phrase "operatively linked" as used herein means that the linkage does not interfere with the ability of either of the linked groups to function as described; e.g., to function as a T or B cell determinant. Thus, operatively linking not only includes covalent linkages, but also includes linkages capable of inducing intermolecular/intrastructural T helper cell function.

The phrase "pathogen related" as used herein designates a polypeptide that is capable of inducing the production of antibodies that immunoreact with a pathogen in native form.

The words "polypeptide" and "peptide" are used interchangeably throughout the specification and designate a linear series of amino acids connected one to the other by peptide bonds between the alpha-amino and carboxy groups of adjacent amino acids. Polypeptides can be a variety of lengths, either in their neutral (uncharged) forms or in forms which are salts, and either free of modifications such as glycosylation, side chain oxidation, or phosphorylation or containing these modifications. It is well understood in the art that amino acid sequences contain acidic and basic groups, and that the particular ionization state exhibited by the peptide is dependent on the pH of the surrounding medium when the protein is in solution, or that of the medium from which it was obtained if the protein is in solid form. Also included in the definition are proteins modified by additional substituents attached to the amino acid side chains, such as glycosyl units, lipids, or inorganic ions such as phosphates, as well as modifications relating to chemical conversions of the chains, such as oxidation of sulfhydryl groups. Thus, "polypeptide" or its equivalent terms is intended to include the appropriate amino acid sequence referenced, subject to those of the foregoing modifications which do not destroy its functionality.

The word "protein" designates a polypeptide having about 70 or more amino acid residues.

The words "secrete" and "produce" are often used interchangeably in the art as to cells from which antibody molecules are obtained. Cells that produce antibodies may, however, not secrete those molecules into their environment. Herein, the antibody molecules are secreted and are obtained from the blood stream (humoral antibody). Nevertheless, antibodies are generally referred to as being "produced" in keeping with the phrase utilized in the art.

The phrase "S (or pre-S1, pre-S2 or pre-S) region polypeptide (or protein)" is used herein, as in the art, to refer to the entire designated region of a subtype of the HBsAg protein or a polypeptide having a corresponding amino acid residue sequence. If reference is made to a portion of any of those regions, that reference is explicit, either by stating, for example, that a portion of the S region is referred to or by explicitly designating the particular portion of the sequence, as by indicating the included amino acid residue positions.

The designation "the 25 kilodalton (kd) polypeptides of HBsAg" or "HBsAg 25 kd polypeptide" herein is meant to indicate the S region polypeptide in the glycosylated or nonglycosylated form sometimes also referred to as p25 and gp 28. Similarly, "the 33 kd polypeptide of HBsAg" and "HBsAg 39 kd polypeptide" are used to designate the glycosylated or nonglycosylated forms of those polypeptides, and are also referred to as p33 and p39.

B. Immunogenic HBcAg Conjugates

Applicants have discovered that operatively linking a polypeptide immunogen to HBcAg, particularly HBcAg in particle form, surprisingly increases the immunogenicity of the linked immunogen to an unexpected degree through the operation of HBcAg's previously unknown T cell dependent and T cell independent determinants. Thus, the present invention contemplates an immunogenic polypeptide conjugate comprising a HBcAg protein operatively linked through an amino acid residue side chain to a polypeptide immunogen.

While the HBcAg protein present in the conjugate can be in substantially monomeric form, in preferred embodiments, it is present as an aggregate such as the well known naturally occurring 27 nanometer (nm) core protein particles.

Methods for producing HBcAg proteins in general and the pre-core, core and HBeAg proteins in particular, are well known in the art. For instance, the core protein in the form of 27 nm particles (particulate HBcAg) can be isolated from the blood or liver of individuals chronically infected with HBV. See, for example, Feitelson et al., *J. Virol.*, 43:687–96 (1982). In addition, HBcAg and HBeAg can be produced by a variety of well known recombinant DNA techniques. See, for example, U.S. Pat. No. 4,356,270 to Itakura and U.S. Pat. No. 4,563,423 to Murray et al., respectively, whose disclosures are all incorporated herein by reference.

Methods for operatively linking individual polypeptides through an amino acid residue side chain to form an immunogenic conjugate, i.e., a branched-chain polypeptide polymer, are well known in the art. Those methods include linking through one or more types of functional groups on various side chains and result in the respective polypeptide backbones being covalently linked (coupled) but separated by at least one side chain.

Useful side chain functional groups include epsilon-amino groups, beta- or gamma-carboxyl groups, thiol (—SH) groups and aromatic rings (e.g. tyrosine and histidine). Methods for linking polypeptides using each of the above functional groups are described in Erlanger, *Method of Enzymology*, 70:85 (1980), Aurameas, et al., *Scand. J. Immunol.*, Vol. 8, Suppl. 7, 7–23 (1978) and U.S. Pat. No. 4,493,795 to Nestor et al., whose disclosures are all incorporated herein by reference. In addition, a site-directed coupling reaction, as described in Rodwell et al., *Biotech.* 3, 889–894 (1985), can be carried out so that the biological activity of the polypeptides is not substantially diminished.

Furthermore, as is well known in the art, both the HBcAg protein and polypeptide immunogen can be used in their native form or their functional group content may be modified by succinylation of lysine residues or reaction with cysteine-thiolactone. A sulfhydryl group may also be incorporated into either polypeptide by reaction of amino functions with 2-iminothiolane or the N-hydroxysuccinimide ester of 3-(3-dithiopyridyl) propionate. The polypeptides can also be modified to incorporate spacer arms, such as hexamethylene diamine or other bifunctional molecules of similar size, to facilitate linking.

Any polypeptide immunogen against which antibody production is desired can be linked to HBcAg protein to form an immunogenic conjugate of this invention. In preferred embodiments the polypeptide immunogen is a pathogen related immunogen and the conjugate has the capacity to induce the production of antibodies that immunoreact with the pathogen when injected in an effective amount into an animal. Exemplary immunogens of particular importance are derived from bacteria such as *B. pertussis, S. typosa, S. paratyphoid* A and B, *C. diptheriae, C. tetani, C. botulinum, C. perfringens, B. anthracis, P. pestis, P. multocida, V. cholerae, N. meningitides, N. gonorrhea, H. influenzae, T. palladium*, and the like; immunogens derived from viruses such as polio virus, adenovirus, parainfluenza virus, measles, mumps, respiratory syncytical virus, influenza virus, equine encephalomyeitis virus, hog chloera virus, Newcastle virus, fowl pox virus, rabies virus, feline and canine distemper viruses, foot and mouth disease virus, human and simian immunodeficiency viruses, and the like; rickettsiae immunogen such as epidemic and endemic typhus, and the spotted fever groups, and the like. Immunogens are well known to the prior art in numerous references such as U.S. Pat. Nos. 3,149,036, 3,983,228, and 4,069,313; in *Essential Immunology*, 3rd Ed., by Roit, published by Blackwell Scientific Publications; in *Fundamentals of Clinical Immunology*, by Alexander and Good, published by W. B. Saunders; and in *Immunology*, by Bellanti, published by W. B. Saunders. Particularly preferred pathogen related immunogens are those described in U.S. Pat. Nos. 4,625,015, 4,544,500, 4,545,931, 4,663,436, 4,631,191, 4,629,783 and in Patent Cooperation Treaty International Publication No. WO87/02775 and No. WO87/02892, all of whose disclosures are incorporated herein by reference.

Methods for determining the presence of antibodies to an immunogen in a body sample from an immunized animal are well known in the art.

In preferred embodiments the polypeptide immunogen is a pathogen related immunogen that immunoreacts with, i.e., is immunologically bound by, antibodies induced by the pathogen. More preferably, the pathogen related immunogen is capable of inducing an antibody response that provides protection against infection by the pathogen. Methods for determining the presence of both cross-reactive and protective antibodies are well known in the art.

In preferred embodiments, the pathogen related polypeptide immunogen is the hepatitis B virus surface antigen (HBsAg). As used herein, HBsAg refers to the naturally occurring filamentous and spherical 22 nm particles, the individual major polypeptides and their glycosylated forms that comprise the particles (e.g. p25/gp28, p39/gp42 and gp33/gp36), and synthetic polypeptides that correspond in amino acid sequence to portions of the individual proteins and glycoproteins.

Thus, in one embodiment, the pathogen related immunogen is filamentous or spherical HBsAg. In another embodiment, the pathogen related immunogen is a 33 kilodalton HBsAg protein or a 25 kilodalton HBsAg protein. In another embodiment, the polypeptide immunogen is a synthetic polypeptide that corresponds to a portion of the pre-S region of HBsAg located between an amino-terminal and carboxy-terminal position, respectively, selected from the group consisting of 1-21, 16-27, 32-53, 53-74, 94-105, 94-117, 106-117, 120-140, 120-145, 128-138, 133-139, 133-140, 133-143, 133-145, 135-143, 135-145, 137-143, 133-151 and 153-171. The amino acid residue sequence of the pre-S region of HBsAg is shown in FIG. 2.

In yet another embodiment the polypeptide immunogen corresponds to a portion of the S region of HBsAg located between amino-terminal and carboxy-terminal position, respectively, selected from the group consisting of 110-137, 117-137, 122-137 and 135-155. The amino acid residue sequence of the S region of HBsAg is shown in FIG. 3.

Methods for preparing polypeptide immunogens are described hereinbelow.

C. HBcAg Fusion Proteins

The unexpectedly strong immunogenicity of particulate HBV core protein discovered by Applicants is believed to be the result of a synergistic effect between its T cell independent and T cell dependent characteristics.

As previously discussed, the art has suggested that T cell independency arises as a result of a threshold number of appropriately spaced haptens or epitopes, i.e., a repeating array of identical determinants, being expressed on a relatively high molecular weight molecule. Thus, the present invention contemplates making advantageous use of the repeating molecular structure inherent in particulate core protein to present otherwise T cell dependent polypeptide immunogens in a T cell independent manner, i.e., a T cell independent array.

Fusion proteins are particularly well adapted for accomplishing the purpose of presenting polypeptide immunogens in a T cell independent array. Thus, the present invention contemplates a fusion protein comprising HBV core protein having a polypeptide immunogen, preferably a pathogen related immunogen, inserted between amino acid residues normally adjacent in the natural core protein such that the polypeptide immunogen is expressed in a T cell independent array when the fusion protein forms an ordered aggregate or particle. Preferably, the amino acid residues that form the polypeptide immunogen are substituted for an identical number of core protein amino acid residues that are known to be present on the surface of 22 nm core particles.

Methods for determining the presence of amino acid residue sequences that are present on the surface of a protein or protein particle are well known. Those methods include determining whether or not antibodies induced by a peptide that corresponds in amino acid residue sequence to a portion of the protein immunoreact with the protein particle in native (intact) form. Using that method, it has been found that amino acid residue sequences from about position 14 to about position 35 and from about position 73 to about position 87 are present on the surface of intact core particles. Polypeptides inserted in or substituted for those regions in a fusion protein are therefore present in a T cell independent array on the surface of particles formed by the fusion protein.

Thus, in preferred embodiments, an immunogenic fusion protein of the present invention comprises a polypeptide immunogen consisting essentially of about 10 to about 30 amino acid residues operatively linked by a peptide bond to an amino-terminal flanking sequence and a carboxy-terminal flanking sequence. The amino-terminal flanking sequence consists essentially of about 10 to about 20 amino acid residues having an amino acid residue sequence corresponding in sequence to core protein from about position 1 to about position 35. The carboxy-terminal flanking sequence consists essentially of about 120 to about 160 amino acid residues having an amino acid residue sequence corresponding in sequence to core protein from about position 10 to about position 183. Preferably, the amino-terminal flanking sequence corresponds in sequence to the core protein from about position 1 to about position 15 and the carboxy-terminal flanking sequence corresponds in sequence to the core protein from about position 30 to about position 183.

Also contemplated is an immunogenic fusion protein comprising a polypeptide immunogen consisting essentially of about 10 to about 30 amino acid residues operatively linked by a peptide bond to an amino-terminal flanking sequence and a carboxy-terminal flanking sequence. The amino-terminal flanking sequence consists essentially of about 70 to about 90 amino acid residues having an amino acid residue sequence corresponding in sequence to core protein from about position 1 to about position 90. The carboxy-terminal flanking sequence consists essentially of about 65 to about 85 amino acid residues having an amino acid residue sequence corresponding in sequence to core protein from about position 80 to about position 183.

In another embodiment, the present invention contemplates an immunogenic fusion protein comprising a HBcAg protein operatively linked by a peptide bond to a pathogen-related immunogen, preferably an immunogen that immunoreacts with antibodies induced by the pathogen.

In preferred embodiments, the immunogenic fusion protein comprises the HBV core protein operatively linked by a peptide bond to an amino acid residue sequence that corresponds to a portion of the pre-S region of HBsAg whose amino acid residue sequence is shown in FIG. 2. Also preferred are embodiments wherein core protein is linked to a portion of the S region of HBsAg whose amino acid residue sequence is shown in FIG. 3.

In a further embodiment, the present invention contemplates an immunogenic fusion protein comprising a HBcAg protein operatively linked at its carboxy-terminus by a peptide bond to the amino-terminus of a polypeptide immunogen, preferably a pathogen-related immunogen.

The immunogenic fusion proteins of the present invention can be produced using well known recombinant DNA techniques. The DNA sequences that encode the pre-core, core and HBeAg proteins are known. Similarly, the DNA sequences of many polypeptide immunogens and pathogen related immunogens are known. DNA sequences that encode for HBcAg protein can be appropriately linked to one or more DNA sequences that encode for a polypeptide or pathogen-related immunogen, inserted into an expression vehicle and expressed as a fusion protein of this invention in an appropriate host.

Exemplary disclosures that describe techniques for genetically engineering a DNA sequence that can be used to produce a fusion protein of the present invention can be found in: U.S. Pat. No. 4,428,941 to Galibert et al., U.S. Pat. No. 4,237,224 to Cohen et al.: U.S. Pat. No. 4,273,875 to Manis; U.S. Pat. No. 4,431,739 to Riggs; U.S. Pat. No. 4,363,877 to goodman et al., and Rodriguez & Tait, *Recominant DNA Techniques: An Introduction*, The Bejamin-Cummings Publishing Co., Inc. Menlo Park, Calif. (1983), whose disclosures are incorporated by reference. Further applicable recombinant DNA techniques are discussed hereinbelow.

D. T Cell Stimulating Polypeptides

The studies described hereinbelow have identified two regions of the HBV core protein that contain T cell stimulating epitopes. Those regions correspond to amino acid residue positions from about 1 to about 55 and from about 70 to about 140 from the amino terminus of the ayw subtype core protein sequence shown in FIG. 1. It is believed that HBV core protein regions 1-44 and 70-140 do not contain determinants that surpress T cell activation.

Thus, the present invention contemplates a T cell stimulating polypeptide consisting essentially of about 15 to about 55 amino acid residues having a sequence corresponding to the amino acid residue sequence of the HBV core protein from about position 1 to about position 55 from the amino terminus thereof. Polypeptides p1-20 and p28-52, whose amino acid residue sequences are shown in Table 1 below, are preferred polypeptides that correspond to a portion of the above-described region of the core protein.

TABLE 1

| Peptide Designation | Synthetic Polypeptides<br>Amino Acid residue Sequence |
|---|---|
| p1-20 | MDIDPYKEFGATVELLSFLP |
| p28-52 | RDLLDTASALYREALESPEHCSPHH |
| p70-94 | TWVGVNLEDPASRDLVVSYVNTNMG |
| p85-100 | VVSYVNTNMGLKFRQL |
| p85-96 | VVSYVNTNMGLK |
| p100-120 | LLWFHISCLTFGRETVIEYLV |
| p100-110 | LLWFHISCLTF |
| P120-140 | VSFGVWIRTPPAYRPPNAPIL |
| p120-131 | VSFGVWIRTPPA |
| p129-140 | PPAYRPPNAPIL |
| p125-136 | WIRTPPAYRPPN |

All amino acid residues identified herein are in the natural or L-configuration. In keeping with standard polypeptide nomenclature, [*J. Biol. Chem.*, 243, 3557–59 (1969)], abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| Z | Glx | L-glutamic acid or L-glutamine |
| W | Trp | L-tryptophan |
| R | Arg | L-arginine |
| D | Asp | L-aspartic acid |
| N | Asn | L-asparagine |
| B | Asx | L-aspartic acid or L-asparagine |
| C | Cys | L-cysteine |

In another embodiment, a T cell stimulating polypeptide consists essentially of about 15 to about 70 amino acid residues having a sequence corresponding to the amino acid residue sequence of HBV core protein from about position 70 to about position 140 from the amino terminus thereof. Polypeptides p70-94, p85-100, p85-96, p100-120, p100-110, p120-140, p120-131, p125-136 and p129-140 whose amino acid residue sequences are shown in Table 1 above, are preferred polypeptides that correspond to a protion of the above described region of the core protein.

The T cell simulating polypeptides of the present invention correspond to T cell epitopes expressed by naturally occurring HBV core and HBeAg proteins. As a consequence, those polypeptides can be operatively linked to another immunogen and used to enhance the production of antibodies that immunoreact with the immunogen.

As previously discussed, linkages can be formed in a variety of ways. Particularly useful are a large number of heterobifunctional agents which generate a disulfide link at one functional group end and a peptide link at the other, including N-succidimidyl-3-(2-pyridyldithio) proprionate (SPDP). This reagent creates a disulfide linkage between itself and a cysteine residue in one protein and an amide linkage through the amino on a lysine or other free amino group in the other. A variety of such disulfide/amide forming agents are known. See for example *Immun. Rev.* (1982) 62:185. Other bifunctional coupling agents form a thioether rather than a disulfide linkage. Many of these thioether forming agents are commercially available and include reactive esters of 6-maleimidocaproic acid, 2 bromoacetic acid, 2-iodoacetic acid, 4-(N-maleimido-methyl) cyclohexane-1-carboxylic acid and the like. The carboxyl groups can be activated by combining them with succinimide or 1-hydroxy-2-nitro-4-sulfonic acid, sodium salt. The particularly preferred coupling agent for the method of this invention is succinimmidyl 4-(N-maleimidomethyl) cyclohexane-1-carboxylate (SMCC) obtained from Pierce Company, Rockford, Ill. The foregoing list is not meant to be exhaustive, and modifications of the named compounds can clearly be used.

The applicants demonstrate that HBcAg-specific T cell epitopes can "help" envelope-specific B cell clones produce antibody even though HBcAg-Specific T cell sites and envelope-specific B cell epitopes are present on different molecules within the same particle. Therefore, entrapment of multiple synthetic T cell sites within an artificial particle becomes a good method to concentrate a large number of T cell helper determinants, which will function to elicit Th cell function for antibody production to any B cell epitope present within the same particle. This eliminates the need to covalently link large numbers of T cell and B cell epitopes.

Thus, another method for operatively linking a T cell stimulating polypeptide of this invention and a pathogen related polypeptide of interest includes entrapment within an artificial particulate structure, such as, for example, liposomes and ISCOM's (Immunostimulating complex). The use of liposomes and ISCOMS as vehicles for delivering the effective ingredients of a vaccine are well known in the art, as is their preparation. See, for example, Gregoriadis, *Trends Biotech.*, 3:235–241 (1986) and North et al., *Proc. Natl. Acad. Sci. USA*, 79:7504–08 (1982), for liposome preparation and Morein et al., *Nature*, 308:457–460 (1987) and Dalsgaard, *Arch ges. Virusforsch.*, 44:243–254 (1974) for ISCOM preparation. A liposome or ISCOM of the present invention thus includes, as effective ingredients, a T cell stimulating polypeptide of the present invention, preferably a peptide of Table 1, and a pathogen related polypeptide, preferably HBsAg, and more preferably HBsAg polypeptide p133-140. Other preferred pathogen related polypeptides are the cyclic HBsAg peptides described by Dreesman et al., *Nature*, 295:158–160 (1982), i.e., HBsAg peptides pl17-137 wherein the cys at position 121 has been replaced with a ser, and p122-137 wherein the arg at position 122 has been replaced with a lys.

The T cell stimulating polypeptides of the present invention can be prepared in a number of conventional ways. Because they are short sequences, they can be prepared by chemical synthesis using standard means, either as separate entities or linked end-to-end with a polypeptide immunogen.

Particularly convenient are solid phase techniques (see for example Erikson, B. W. et al., *The Proteins* (1976) v. 2, Academic Press, New York, p. 255). Indeed, automated solid phase synthesizers are commercially available, as are the reagents required for their use. Thus, not only is it possible to mimic the sequence of amino acids in the 1-20, 28-52 and 70-140 regions of the HBV core protein, modifications in the sequence can easily be made by substitution, addition or omission of appropriate residues. Particularly convenient modifications, as set forth above, include the addition of a cysteine residue at the carboxy terminus to provide a sulfhydryl group for convenient linkage to the polypeptide immunogen. In addition, spacer elements, such as an additional glycine residue may be incorporated into the sequence between the linking amino acid at the C-terminus and the remainder of the peptide.

Also because the desired sequences are relatively short, recombinant techniques to produce these peptides, alone or in combination with a polypeptide immunogen amino acid residue sequence, are particularly useful. As previously discussed, DNA sequences that encode for HBcAg and a variety of polypeptide immunogens are known in the art. The coding sequence for peptides of the length contemplated herein can easily be synthesized by chemical techniques, for example, the phosphotriester method of Matteucci, M. et al., *J. Am. Chem. Soc.* (1981) 103:3185. Of course, by chemically synthesizing the coding sequence, any desired modification can be made simply by substituting the appropriate bases for those encoding the native peptide sequence. The coding sequence can then be provided with appropriate linkers and ligated into expression vectors now commonly available in the art, and the regulating vectors used to transform suitable hosts to produce the desired protein.

A number of such vectors and suitable host systems are now available. For example promoter sequences compatible with bacterial hosts are provided in plasmids containing convenient restriction sites for insertion of the desired coding sequence. Typical of such vector plasmids are, for example, pUC8, and pUC13 available from Messing, J., at the University of Minnesota; (see, e.g., Messing et al., *Nucleic Acids Res.* (1981) 9:309) or pBR322, available from New England Biolabs. Suitable promoters include, for example, the beta-lactamase (penicillinase) and lactose (lac) promoter systems (Chang, et al., *Nature* (1977) 198:1056 and the tryptophan (trp) promoter system (Goeddel, D., et al., *Nucleic Acids Res.* (1980) 8:4057). The resulting expression vectors are transformed into suitable bacterial hosts using the calcium chloride method described by Cohen, S. N., et al., *Proc. Natl. Acad. Sci. USA* (1972) 69:2110. Successful transformants may produce the desired polypeptide fragments at higher levels than those found in strains normally producing the intact pili. Of course, yeast or mammalian cell hosts may also be used, employing suitable vectors and control sequences.

Thus, in one embodiment, a T cell stimulating polypeptide of the present invention, preferably a polypeptide shown in Table 1, is operatively linked to HBsAg, preferably at the amino- or carboxy-terminus of HBsAg, to form a fusion protein, preferably a fusion protein that forms filaments or particles.

E. Composite Polypeptide Immunogen

In one embodiment, a composite polypeptide immunogen comprises a T cell stimulating polypeptide of this invention, preferably a polypeptide as shown in Table 1, operatively linked to a pathogen related polypeptide. Thus, in one embodiment, a composite polypeptide immunogen comprises at least 20 amino acid residues that includes a T cell stimulating polypeptide consisting essentially of about 15 to about 70 amino acid residues having a sequence corresponding to the amino acid residue sequence of core protein from about position 70 to about position 140 from the amino terminus thereof operatively linked to a polypeptide immunogen. In preferred embodiments, the T cell stimulating polypeptide is p70-94, p85-100, p85-96, p100-120, p100-110, p120-140, p120-131 or p129-140, as shown in Table 1. More preferably, the composite polypeptide immunogen comprises p100-120 operatively linked to particulate HBsAg through an amino acid residue side chain, i.e., the composite immunogen is a particulate HBsAg-p100-120 conjugate.

In another embodiment, composite polypeptide immunogen of the present invention is characterized as comprising of a T cell stimulating polypeptide of this invention operatively linked in end-to-end manner by a peptide bond to a pathogen related polypeptide to form a composite amino acid residue sequence having at least about 15 residues to about 70 residues.

Further preferred is a composite immunogen comprising p100-120 or p120-140 operatively linked by a peptide bond to an amino acid residue sequence, selected from the group of sequences, taken from left to right and in the direction of amino-terminus to carboxy-terminus, represented by the formulae:

DPRVRGLYFPAGG, and

DPRVRGLY.

The composite polypeptide immunogens of the present invention can be produced by the before described well known synthetic and recombinant DNA methods.

F. Methods for Enhancing Immunogenicity

The HBcAg T cell epitope containing polypeptides can be used to enhance the immunogenicity of a polypeptide immunogen, preferably a pathogen related immunogen. Broadly, a method for accomplishing that purpose comprises operatively linking an HBcAg T cell epitope containing polypeptide to the immunogen.

In particular, the present invention contemplates a method of enhancing the immunogenicity of a polypeptide immunogen comprising operatively linking the immunogen to HBcAg, preferably core protein and more preferably particulate core protein, through an amino acid residue side chain.

A method of enhancing the immunogenicity of a pathogen-related immunogen comprising linking the immunogen to HBcAg, preferably core protein, by a peptide bond is also contemplated. Where core protein is used, linkage preferably occurs at the carboxy-terminus of the core protein.

Further contemplated is a method of enhancing the immunogenicity of a polypeptide immunogen comprising operatively linking said polypeptide immunogen to a T cell stimulating polypeptide consisting essentially of about 15 to about 70 amino acid residues having a sequence corresponding to the amino acid residue sequence of HBcAg from about position 70 to about position 140 from the amino terminus thereof.

The methods for enhancing immunogenicity described above can be accomplished using the production and linking techniques described hereinbefore.

G. Vaccines

In another embodiment, an immunogenic HBcAg conjugate, fusion protein, T cell stimulating polypeptide or composite polypeptide of the present invention is used in a pharmaceutically acceptable composition that, when administered in an effective amount, is capable of inducing antibodies that immunoreact with polypeptide or pathogen-related immunogen that corresponds in amino acid residue sequence to the operatively linked polypeptide or pathogen related immunogen used in the vaccine.

The preparation of vaccines which contain peptide sequences as active ingredients is also well understood in the art. Typically, such vaccines are prepared as injectables, either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents or adjuvants which enhance the effectiveness of the vaccine.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycos or triglycerides; such suppositories may be formed from mixtures containing the active ingredient in the rage of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders and contain 1.0%-95% of active ingredient, preferably 2.5-70%.

The polypeptides can be formulated into the vaccine as neutral or salt forms. Pharmaceutically acceptable salts, include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, capacity of the subject's immune system to synthesize antibodies, and degree of protection desired. Precise amounts of active ingredient required to be administered depend on the judgment of the practitioner and are peculiar to each individual. However, suitable dosage ranges are of the order of several hundred micrograms active ingredient per individual. Suitable regimes for initial administration and booster shots are also variable, but are typified by an initial administration followed in one or two week intervals by a subsequent injection or other administration.

H. Therapeutic Methods

A characteristic of HBV infection is vigorous IgM anti-HBcAg antibody production, which occurs early during the acute stage of infection. Similarly, many chronically infected patients also maintain IgM anti-HBcAg, although usually at lower titers. In contrast, HBsAg elicits a relatively weak IgM response during infection and after vaccination. In a comprehensive serological study of IgM anti-HBcAg production during HBV infection, Gerlich et al., *J. Infect. Dis.*, 142:95 (1980), reported variation in the kinetics of IgM persistence in resolving acute hepatitis, and a very slow decrease or even increase in IgM anti-HBcAg in patients progressing to chronicity.

Furthermore, in chronic hepatitis B patients, in whom viral replication was reactivated by prednisone therapy, the IgM anti-HBc levels were dramatically elevated with no change in IgG titers. These findings are consistent with the notion that IgM anti-HBc production in HBV infection may be T cell-independent and, furthermore, that the switch from predominantly IgM to high-titers of IgG anti-HBc requires T cell helper function, which may be variably present from patient to patient and be defective in patients who progress to chronicity. This would explain the slow decline in IgM anti-HBc titers during the first 1 to 2 years of chronic infection. Since T cell recognition of HBcAg and HBeAg is highly crossreactive, it is believed that T cell help for IgG anti-HBc production would also help anti-HBe production.

Thus, the present invention contemplates a method of potentiating the T cell response to HBeAg in an individual infected with HBV comprising administering an effective amount of a T cell stimulating polypeptide of the present invention. Preferably, the T cell stimulating polypeptide consists essentially of about 15 to about 70 amino acid residues having a sequence corresponding to the amino acid residue sequence of the HBV core protein from about position 70 to about position 140 from the amino terminus thereof.

EXAMPLES

The following examples are intended to illustrate, but not limit, the present invention.

1. Synthesis of Polypeptides

The polypeptides corresponding to the various HBcAg regions utilized herein were chemically synthesized by solid phase methods as described in Merrifield et al., (1963) *J. Am. Chem. Soc.*, 85:2149. The solid phase method of polypeptide synthesis was practiced utilizing a Vega 250 Peptide Synthesizer and an Applied Biosciences 430A Peptide Synthesizer, available commercially from Vega Biotechnologies, Inc., Tucson, Ariz. and Applied Biosystems, Foster City, Calif., respectively. The composition of each polypeptide was confirmed by amino acid analysis.

Briefly, in preparing a synthetic polypeptide by the above solid phase method, the amino acid residues are linked to a resin (solid support) through an ester linkage from the carboxy-terminal residue. When the polypeptide is to be linked to a carrier or another polypeptide via a Cys residue or reacted via terminal Cys residues, it is convenient to utilize that Cys residue as the carboxy-terminal residue that is ester-bonded to the residue.

The alpha-amino group of each added amino acid is typically protected by a tertiary-butoxycarbonyl (t-BOC) group prior to the amino acid being added into the growing polypeptide chain. The t-BOC group is then removed prior to addition of the next amino acid to the growing polypeptide chain.

Reactive amino acid side chains were also protected during synthesis of the polypeptides. Usual side-chain protecting groups were used for the remaining amino acid residues as follows: O-(p-bromobenzyloxycarbonyl) for tyrosine; O-benzyl for threonine, serine, aspartic acid and glutamic acid; 4 methylbenzl and S-methoxybenzyl for cysteine, dinitrophenyl for histidine; 2-chlorobenzoxycarbonyl for lysine and tosyl for arginine.

The peptides synthesized on the Applied Biosystems Model 430A Peptide Synthesizer were made using the symmetrical anhydride method of Hagenmaier, H., and Frank, A. (1982), *Hoppe-Seyler's Z. Physiol. Chem.*, 353:1973. The DCC in situ method, as described by Merrifield et al. (1963) *J. Amer. Chem. Soc.*, 85:2149 was used to synthesize the peptides from the Vega 250 Peptide Synthesizer. Repeat coupling of the incoming protected amino acid was sometimes necessary to effect complete coupling efficiency. All coupling reactions were more than 99% complete by the quantitative ninhydrin test of Sarin (1981), *Analytical Chemistry*, 117:147

After preparation of a desired polypeptide, a portion of the resulting, protected polypeptide (about 1 gram) was treated with two milliliters of anisole, and anhydrous hydrogen fluoride, about 20 milliliters, was condensed into the reaction vessel at dry ice temperature to form an admixture. The resulting admixture was stirred at about 4 degrees C. for about one hour to cleave the protecting groups and to remove the polypeptide from the resin. After evaporating the hydrogen fluoride at a temperature of 4 degrees C. with a stream of $N_2$ the residue was extracted with anhydrous diethyl ether three times to remove the anisole, and the residue was dried.

The dried material was extracted with the 5 percent aqueous acetic acid (3 times 50 milliliters) to separate the free polypeptide from the resin. The extract-containing solution was lyophilized to provide the polypeptide.

2. Preparation of Polymers

A polypeptide polymer of this invention can be prepared by synthesizing a polypeptide of this invention, as discussed in Example 1, and including cysteine residue at both the amino- and carboxy-termini to form a "di-Cys-terminated" polypeptide in un-oxidized, reduced form. After synthesis, in a typical laboratory preparation, 10 milligrams of the diCys polypeptide (containing cysteine residues in unoxidized form) are dissolved in 250 milliliters (ml) of 0.1 molar (M) ammonium bicarbonate buffer. The dissolved diCys-terminated polypeptide is then air oxidized by stirring the resulting solution gently for a period of about 18 hours in the air at ambient room temperature, or until there is no detectable free mercaptan by the Ellman Test. Ellman, *Arch. Biochem. Biophys.*, 82:70–77 (1959).

The polymer so prepared contains a plurality of the synthetic, random copolymer polypeptide repeating units that are bonded together by oxidized cysteine (cystine) residues.

3. Coupling to Carriers

Synthetic polypeptide immunogens can be coupled to HBcAg as immunogenic carrier by the method described in Liu et al., *Biochem.*, 80:690 (1979). Briefly 4 milligrams (mg) of the carrier (HBcAg) are activated with 0.51 mg of m-maleimidobenzoyl-N-hydroxysuccinimide ester. The activated HBcAg is subsequently reacted with 5 mg of the polypeptide immunogen through an amino- or carboxy-terminal cysteine to provide a conjugate containing about 10 to about 35% by weight polypeptide immunogen.

4. Comparison of the immunogenicity of HBcAg with HBsAg

A number of inbred murine strains, including a series of H-2-congenics, were immunized with 4 ug of rHBcAg or HBsAg (both particulate antigens) in complete Freunds adjuvant (CFA), and primary IgG antibody responses were analyzed by solid-phase radioimmunoassays (RIA) of approximately equal sensitivities. The results of these assays correlated with results obtained with commercially available anti-HBsAg and anti-HBc assays (Abbott), and were of equal to greater sensitivity. All strains immunized with HBcAg showed a vigorous, primary, IgG anti-HBcAg response (Table 2).

TABLE 2

Comparison of Primary Antibody Responses After Immunization With HBsAg and HBcAg.

| Strain[1] | H-2[2] | Anti-HBs (titer) | Anti-HBc (titer)] |
|---|---|---|---|
| B10 | b | 256 | 40,960 |
| B10.D2 | d | 1,024 | 81,920 |
| B10.S | s | $0^{-3}$ | 163,840 |
| B10.BR | k | 32 | 163,840 |
| B10.M | f | $0^{-3}$ | 20,480 |
| C3H.Q | q | 2,048 | 327,680 |
| Balb/c | d | 1,024 | 327,680 |

[1]The inbred murine strains B10, B10.D2, B10.S, B10.BR, B10.M, C3H.Q, and Balb/c were obtained from the breeding colony at the Research Institute of Scripps Clinic, La Jolla, CA. Female mice between six and eight weeks of age were used in all studies.
[2]Groups of five mice from each strain were immunized with 4.0 mg of HBsAg or HBcAg in CFA, and pooled sera were analyzed by solid phase RIA for IgG antibodies of the indicated specificities at day 24. Data are expressed as the reciprocal of the highest serum The influence of H-2-linked genes on the anti-HBc response is apparent, i.e., the responses of the B10.S, B10.BR strains were greater than the responses of B10, B10.D2, B10.M, although no nonresponder strains were identified. The anti-HBcAg responses were significantly greater (at least 80-fold) than the anti-HBsAg responses in all strains tested. Furthermore, high-titered anti-HBcAg persists in these mice a year after this single HBcAg dose. The comparative magnitudes of the primary anti-HBcAg and anti-HBs responses, and the lack of nonresponsiveness to HBcAg are, in general, consistent with the human immune responses to these HBV antigens during the course of HBV infection.

5. T Cell Independency of HBcAg

The ability of HBcAg to activate B cells directly, i.e., act as a T cell independent immunogen, was examined. Groups of 5 B10.BR euthymic (+/+) or B10.BR athymic (nu/nu) were immunized intraperitoneally with a single dose of either 0.5, 1.5 or 4.0 micrograms (ug) of *E. coli*-derived, recombinant HBcAg (rHBcAg; Biogen).

At 10 and 24 days after immunization, sera were collected, pooled, and analyzed for the presence of anti-HBcAg antibodies using the solid phase RIA described in Example 4.

Figure 4A:
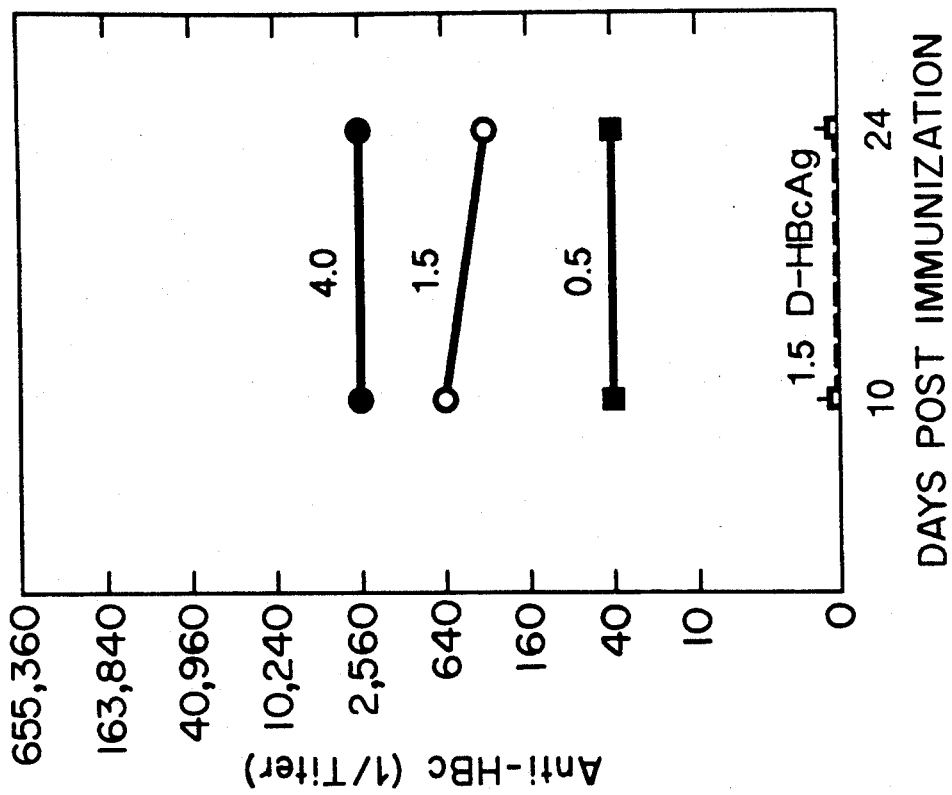
Figure 4B:
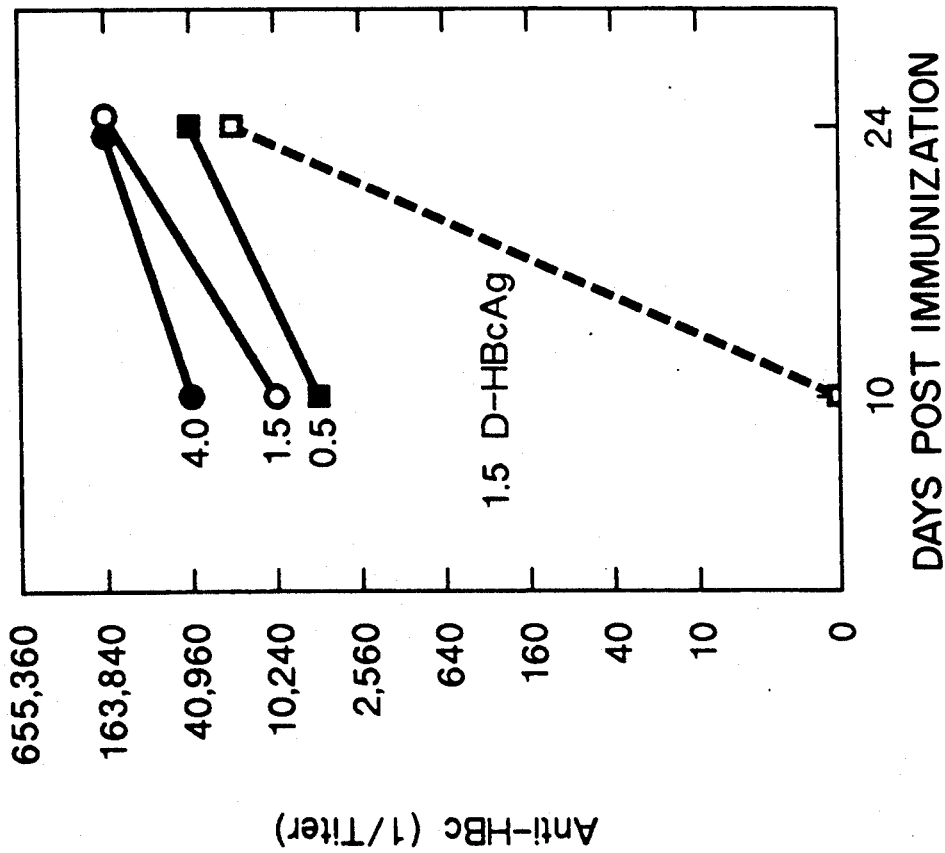

As shown in FIG. 4, Panel A, the B10.BR +/+ mice produced dose-dependent, anti-HBcAg antibody at 10 days and a 4 to 16-fold increase in anti-HBcAg titer at 24 days. However, the B10.BR nu/nu mice also produced dose-dependent, anti-HBcAg antibody at 10 days after immunization (FIG. 4, Panel B), but showed no increase in the anti-HBcAg titer at 24 days. Complete Freund's adjuvant was not required, since B10.BR nu/nu mice immunized with HBcAg in incomplete adjuvant also produced anti-HBc, although of lesser titer. In addition, anti-HBc production by athymic mice was not unique to *E. coli*-derived rHBcAg, since immunization with yeast-derived rHBcAg also elicited an equivalent response.

6. T Cell Sensitivity to HBcAg

The sensitivity of T cells to HBcAg stimulation was examined. Groups of 4 mice of the strains were immunized with 4 micrograms (ug) of HBcAg in CFA in the hind footpads, and 8 days later draining lymph node cells were harvested and cultured in vitro with varying concentrations of HBcAg. Supernatants were collected after 24 hours of culture and assayed for IL-2 production by a standard IL-2 bioassay using the NK-A, IL-2-dependent cell line. IL-2 production is well known in the art to be a sensitive measure of T cell activation.

Figure 5:
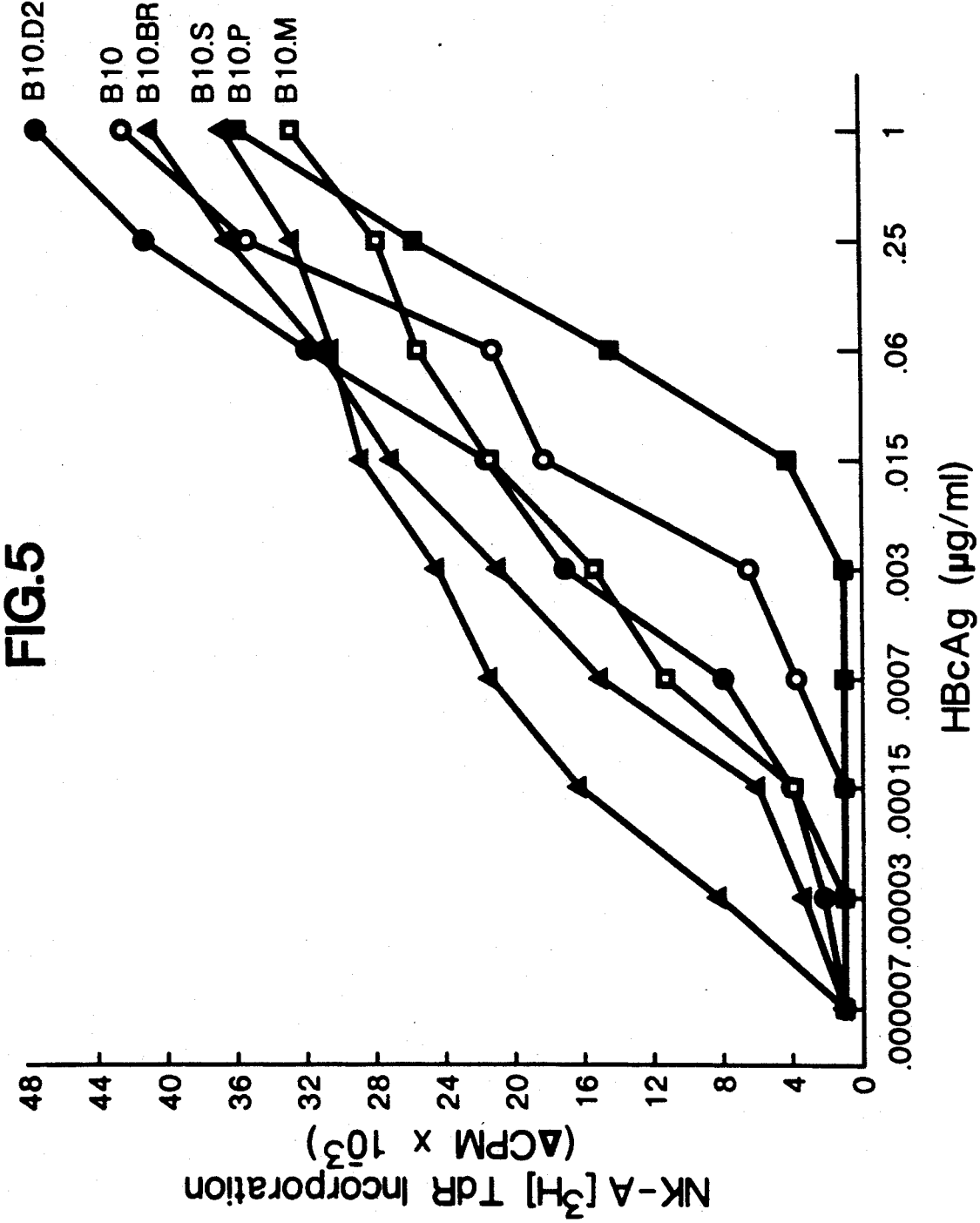

FIG. 5 illustrates the results of this study. Comparison of those results for the various H-2 congenic strains in terms of the lowest concentration of HBcAg required to elicit significant IL-2 production yields a similar classification as that observed by in vivo antibody production (i.e., high, low and intermediate).

Surprisingly, the high responding strains demonstrated HBcAg-specific, T cell activation at an HBcAg concentration as low as 0.03 nanograms per milliliter (ng/ml), which is equivalent to a concentration of 0.0014 nanomolar (nM). The applicants are not aware of another antigen which demonstrates this degree of efficiency in terms of activating T cells.

7. Immunization Dose Response

Effect of immunization dose on the HBcAg-specific T cell proliferative response was also studied. Groups of 4 C3H.Q mice were immunized by injecting either 12, 8, 4 or 1 ug of HBcAg in CFA into the hind footpads. Draining popliteal lymph node cells were aseptically removed from each mouse and teased to yield a single cell suspension. The cells were washed twice with a balanced salt solution (BSS) containing phosphate-buffered saline (pH 7.2). The cells were resuspended in Click's medium containing BSS, L-glutamine, sodium pyruvate, antibiotics, 2-mercaptoethanol, essential and non-essential amino acids and vitamins. [See Click et al., (1972) *Cell. Immunol.*, 3:264.] Click's medium was modified by the addition of 10 millimolar (mM) HEPES (n-2-hydroxyethyl piperazine-N'-2-ethanesulfonic acid) and gentamycin (10 ug/ml), and by the substitution of 0.5 percent syngeneic normal mouse serum for fetal calf serum.

The antigens were assayed in culture over a dose range of 0.00015–0.25 ug/ml of an HBcAg preparation.

Viable lymph node cells ($5 \times 10^5$) in 0.1 ml of medium were placed in flat-bottom microtiter wells (Falcon 3072, Falcon Plastics, Inc.) with: (a) 0.1 milliliter of medium containing various concentrations of a HBcAg preparation.

Cultures were maintained for five days at 37 degrees C. in a humidified atmosphere containing 5 percent carbon dioxide in air.

On the fourth day, each culture was admixed and maintained (incubated) with one microcurie (uCi) $^3$H-thymidine ($^3$HTdR) (6.7 Ci/millimole, New England Nuclear, Boston, Mass.) for 16 hours before harvesting. Cells were harvested onto filter strips and proliferation was determined by the incorporation of $^3$HTdR into DNA. The data are expressed as counts per minute (cpm) corrected for background proliferation in the absence of antigen. It was demonstrated previously that the HBsAg-specific proliferation response of draining PLN cells harvested up to 13 days post-immunization was due to proliferating T cells; Milich et al., *J. Immunol.*, 130:1401 (1983). Therefore, unfractionated PLN cells were used in analysis described herein.

Figure 6:
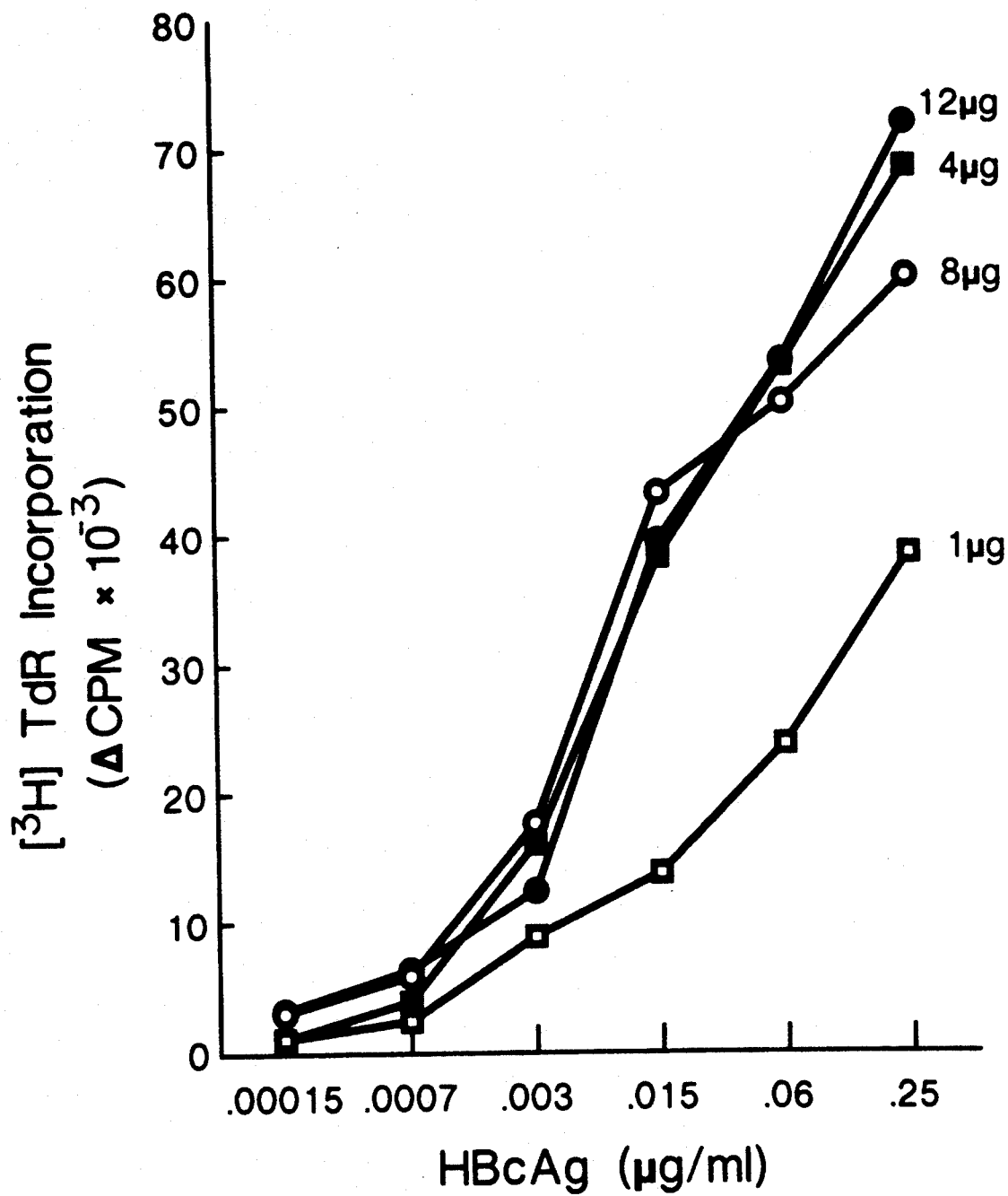

The results of this study, shown in FIG. 6, indicated that an in vivo dose as low as 1 ug was sufficient to induce significant T cell activation. By comparison an HBsAg dose of 16 ug is required to elicit a similar T cell response. In most nonparticulate, antigen systems 50-100 ug doses are usually required to induce significant T cell responses. Therefore, applicants have discovered that HBcAg has an unexpectedly high capacity to stimulate T cell activation in vivo.

8. Evaluation of Particulate HBcAg

To determine if T cell independence required HBcAg to be particulate, groups of 5 each of B10.BR euthymic (+/+) or B10.BR athymic (nu/nu) mice were immunized intraperitoneally with a single dose of 1.5 ug of denatured HBcAg (D-HBcAg) in CFA. HBcAg was denatured by treatment with a final concentration of 0.1% SDS and 0.1% 2-mercaptoethanol for 2 hours at 37° C. The resulting preparation was immunoreactive with monoclonal antibodies to HBeAg, but lost greater than 95% of its immunoreactivity with monoclonal antibodies to HBcAg. Monoclonal antibodies [Takahashi et al., *J. Immunol.*, 130:2903 (1982)] were provided by M. Mayumi (Jichi Medical School, Japan). At 10 and 24 days after immunization, sera were collected, pooled, and analyzed for anti-HBcAg activity by solid-phase RIA as described in Example 4.

The results of this study are illustrated in FIG. 4, Panels A and B so that they may be compared to the results obtained in Example 5 wherein nondenatured (native) HBcAg was used as immunogen. In FIG. 4, Panel A, it can be seen that although D-HBcAg was significantly less immunogenic than native HBcAg in B10.BR +/+ mice, antibodies reactive with denatured HBcAg were detectable by day 24.

In contrast, Panel B of FIG. 4 shows that B10.BR nu/nu mice did not respond to D-HBcAg, indicating that the response to D-HBcAg was T cell-dependent unlike the HBcAg-specific response (FIG. 4, Panels A and B). Since D-HBcAg bound monoclonal anti-HBeAg, and expressed less than 5% of the original HBcAg antigenicity, D-HBcAg represented HBeAg as an antigen. However, a caveat to the assumption that D-HBcAg also represents HBeAg as an immunogen is the possibility that naturally occurring HBeAg may have a different subunit structure (i.e. degree of polymerization) as opposed to D-HBcAg.

9. Comparison of the In Vivo Response Kinetics to HBcAg and HBsAg

To examine the relative kinetics of anti-HBcAg and anti-HBsAg antibody production in vivo and to demonstrate that the HBcAg preparation possessed no inherent adjuvanticity, groups of 5 Balb/c euthymic (+/+) and athymic (nu/nu) mice were immunized intraperitoneally with a mixture of rHBcAg (8 ug) and HBsAg (8 ug). Serum samples before and 6, 12 and 24 days after immunization were pooled and analyzed for the presence of anti-HBcAg antibodies by solid phase RIA as described in Example 4, and for the presence of anti-HBsAg antibodies as described in Milich et al., *J. Immunol.* 1279:320 (1982).

Figure 7B:
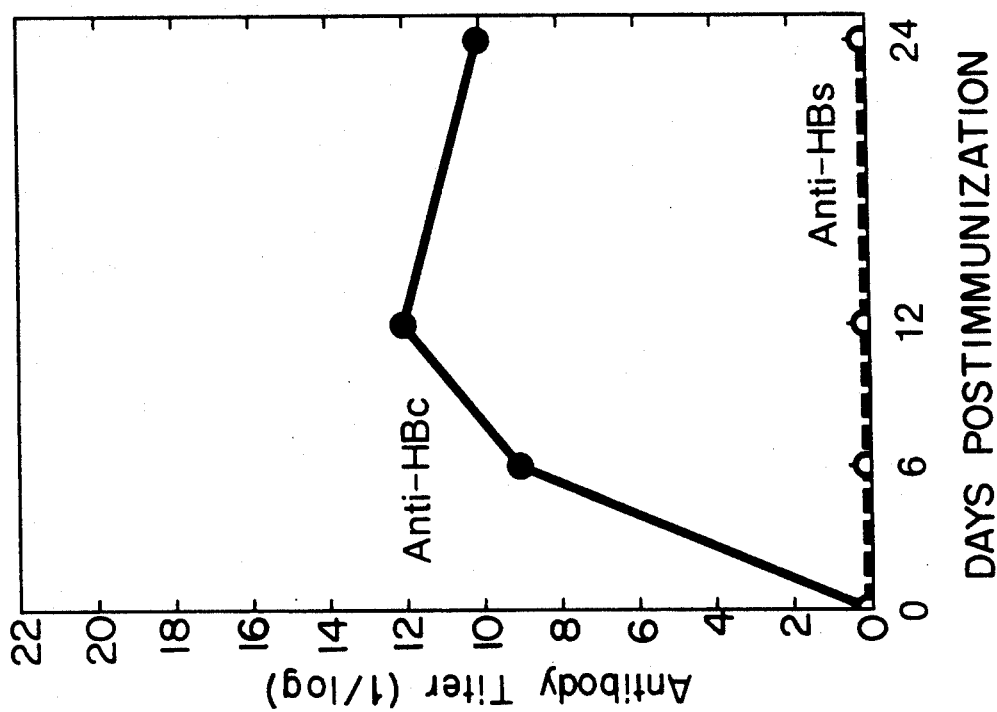
Figure 7A:
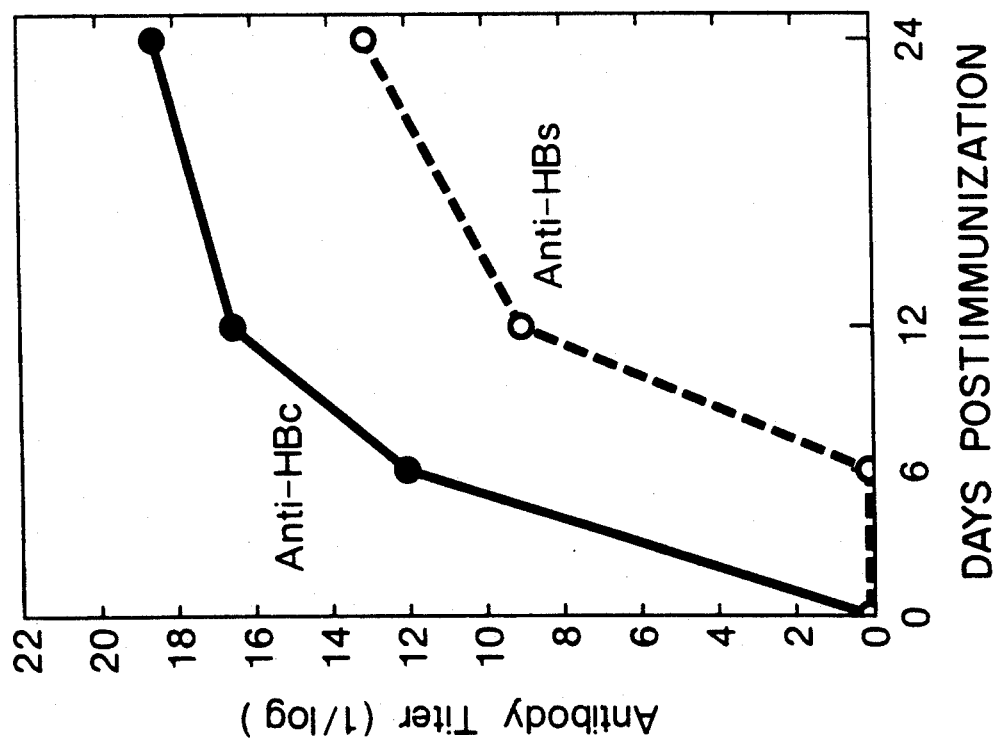

The results of this study, illustrated in FIG. 7 Panels A and B, show that the Balb/c +/+ mice produced anti-HBcAg antibodies as early as 6 days after immunization and the titer continued to rise through day 24. However, the presence of anti-HBsAg antibodies were not detected until day 12 and was of significantly lower titer throughout the observation period (FIG. 7, Panel A). In contrast, the Balb/c nu/nu mice produced no anti-HBsAg at all, but produced anti-HBcAg as early as day 6; the titer peaked at day 12 and began to decline by day 24 (FIG. 7, Panel B).

The lack of an anti-HBsAg response in Balb nu/nu mice is consistent with the T cell-dependent nature of HBsAg as previously described Roberts et al., *Nature*, 254:606 (1975). However, it is clear from this study and that described in Examples 5-8 that HBcAg can function as a T cell-independent antigen.

10. Comparison of T Cell Response to HBcAg and HBeAg

The possibility that T cell responses specific for HBcAg and D-HBcAg (i.e., HBeAg) might account for the differential immunogenicity of these two antigens was examined.

Groups of four C$_3$H.Q mice were primed in the hind footpads with either 4.0 ug of HBcAg or 4.0 ug of denatured HBcAg (D-HBcAg) in CFA. After 8 days, draining lymph node cells were harvested, pooled, and cultured with varying concentrations of HBcAg, sonicated HBcAg (D$_s$-HBsAg), an HBcAg/HBeAg-specific synthetic peptide representing residues 100–120, or media alone. The D$_s$-HBcAg was sonicated to the extent that it was totally unreactive with anti-HBc and anti-HBe monoclonal antibodies. T cell activation was measured by antigen-induced, IL-2 production. Twenty-four hours after the initiation of the in vitro cultures, supernatants were collected and assayed for IL-2 content as described in Example 5.

Figure 8B:
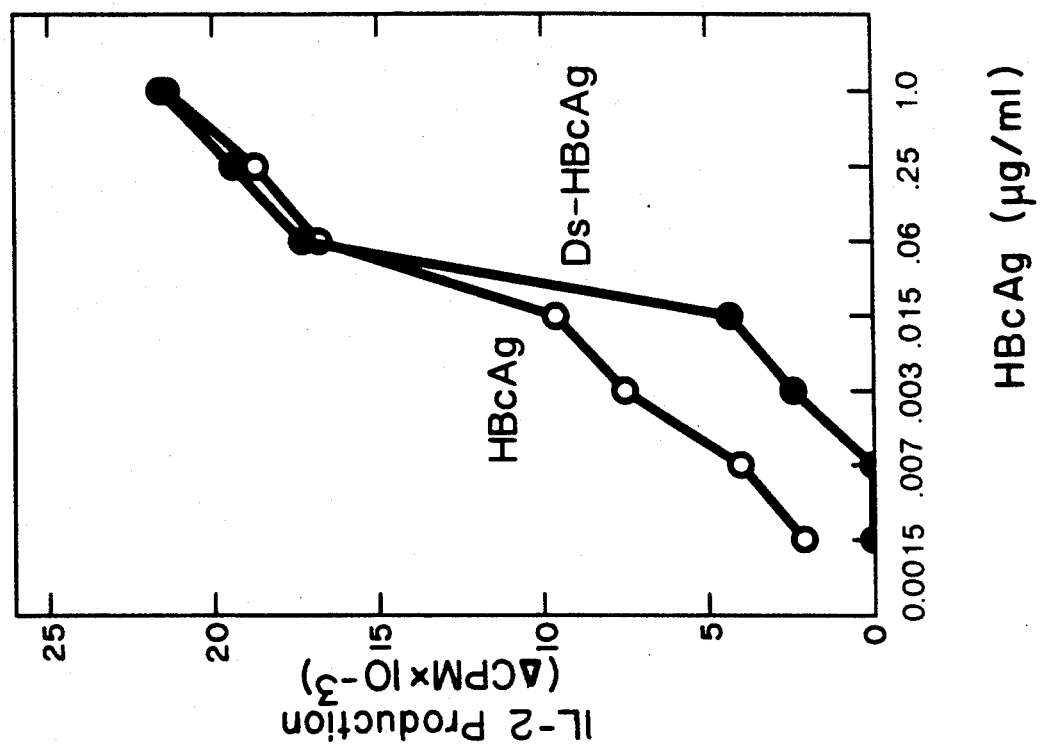
Figure 8A:
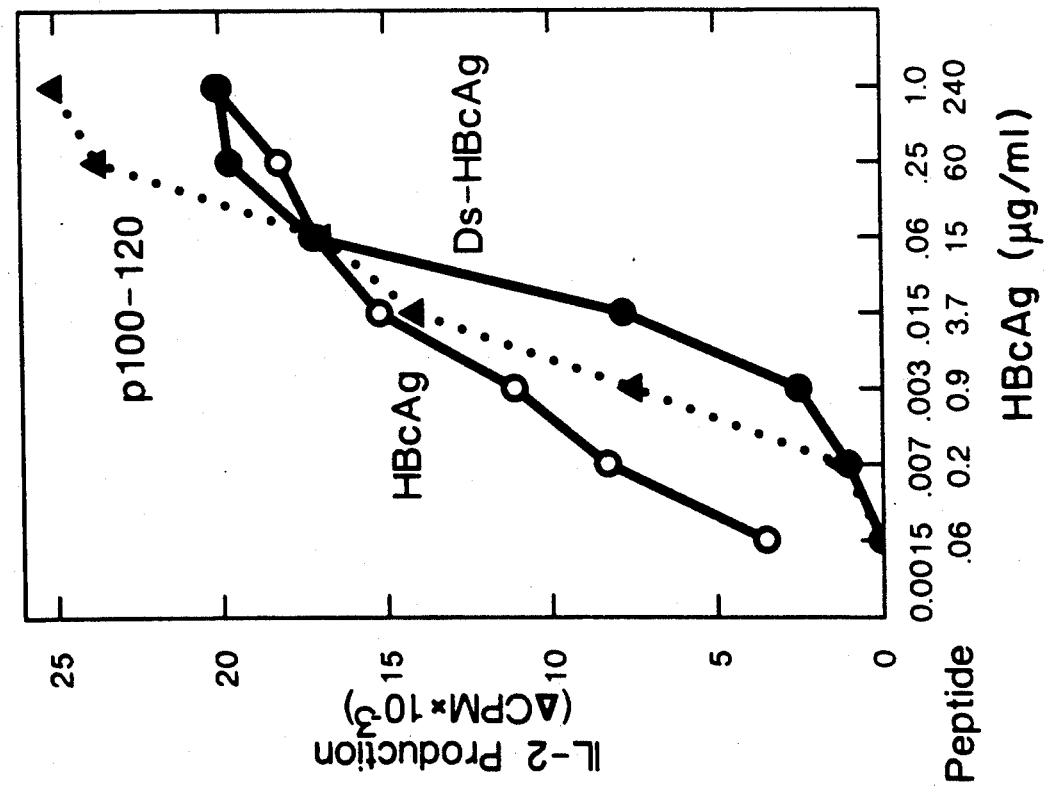
Figure 9A:
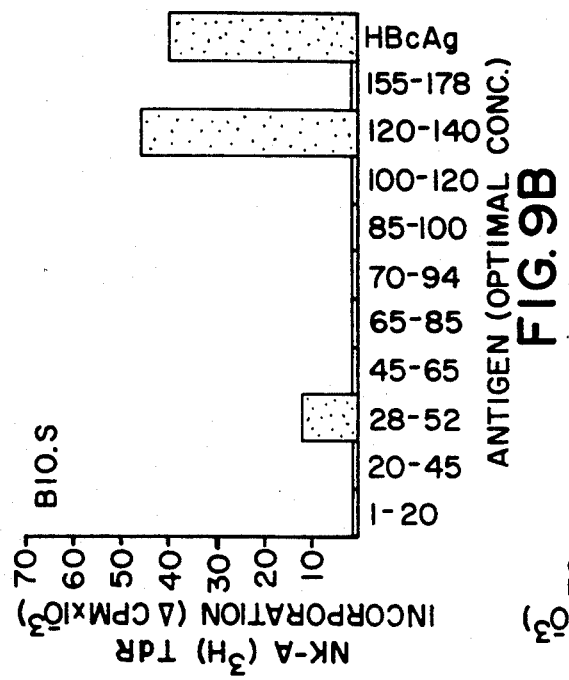
Figure 9B:
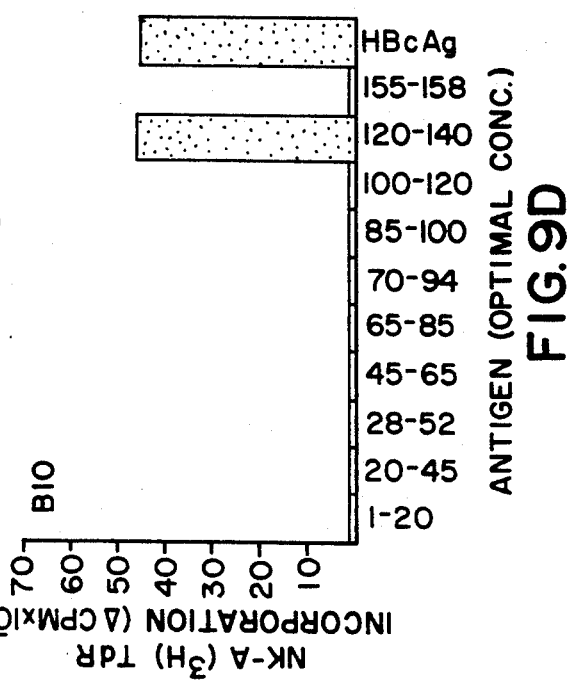
Figure 9C:
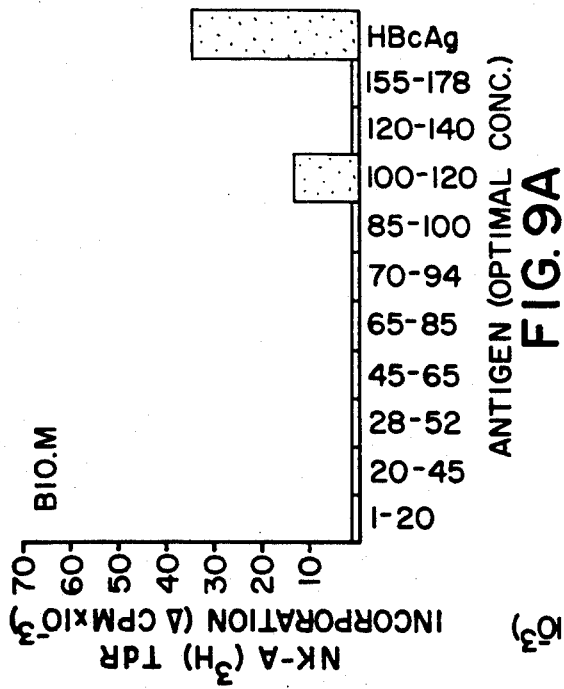
Figure 9D:
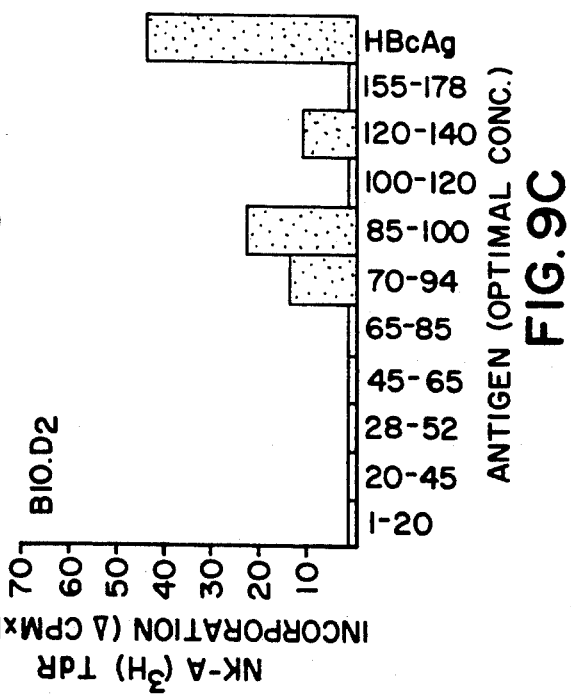
Figure 9E:
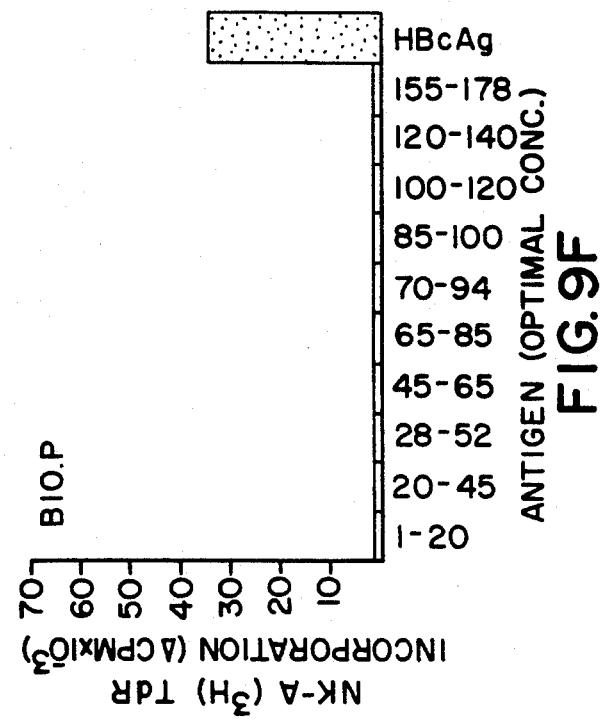
Figure 9F:
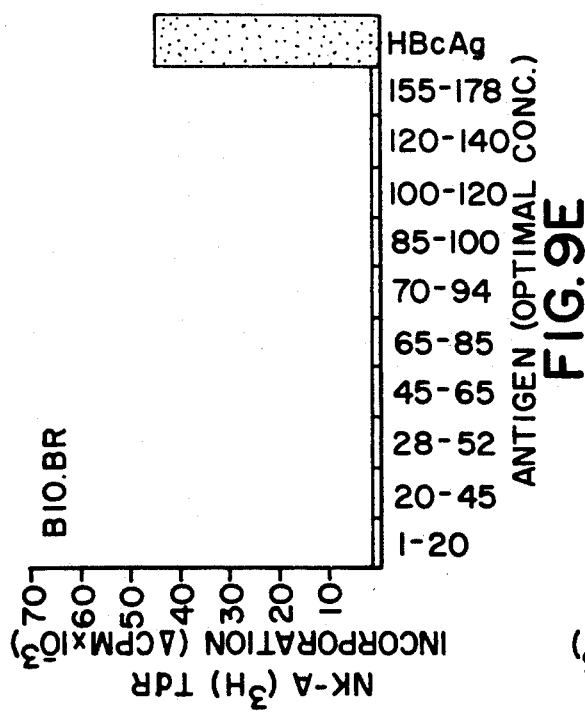
Figure 9G:
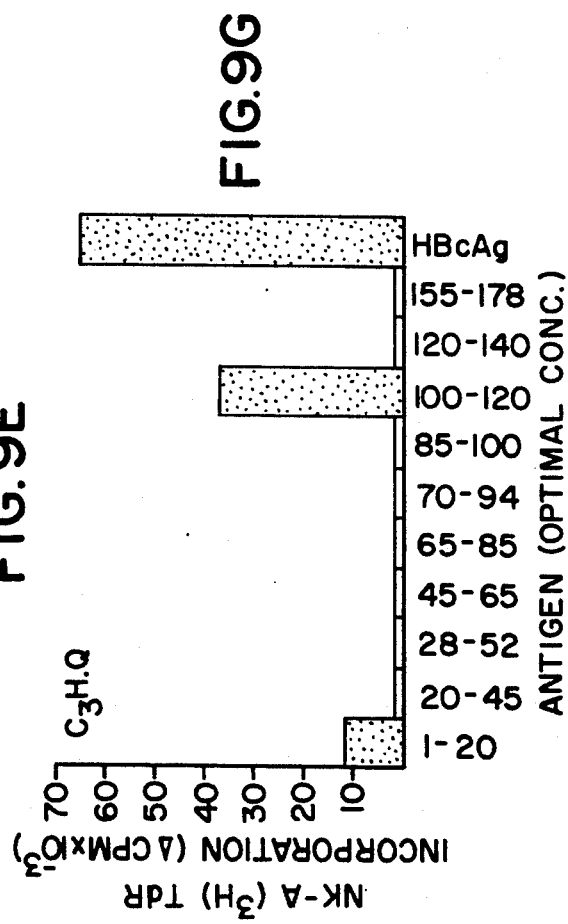

As shown in FIG. 8, Panels A and B, the responses of HBcAg-primed T cells to both HBcAg and D$_s$-HBcAg were equivalent at the high-end of the dose response curve (0.06 to 1.0 mg/ml). The particulate form was more efficient at the low-end of the dose response curve. Surprisingly, HBcAg elicited IL-2 production by HBcAg-primed T cells at an antigen concentration as low as 0.15 ng/ml. (FIG. 8, Panel A).

In the reciprocal experiment, D-HBcAg-primed T cells recognized rHBcAg and D$_s$-HBcAg in a manner similar to rHBcAg-primed T cells (FIG. 8 Panel B). Since the rHBcAg particle was recognized better, regardless of the priming antigen, the particulate form of the antigen may be more efficiently phagocytosed and presented to T cells. Similarly, the ability of HBeAg to activate rHBcAg-primed T cells was examined and it was found that unpurified, rHBeAg can activate HBcAg-primed T cells.

The above described studies indicate that HBcAg and HBeAg are virtually indistinguishable at the T cell level, i.e., they both express the same T cell stimulating epitopes. This is the case even though HBcAg and HBeAg are serologically distinct. In support of this conclusion, a 21-residue synthetic peptide representing residues 100-120 within the HBcAg/HBeAg (synthetic polypeptide p100-120 as described in Table 1) overlapping sequence was found to be capable of activating HBcAg-primed T cells in vitro. (FIG. 8, Panel A).

11. Identification of T cell Stimulating Polypeptides

T cell determinants within the HBcAg/HBeAg overlapping sequence were localized using synthetic polypeptides. Groups of 4 mice each of the C3H.Q, B10.S, B10.D2, B10, B10.M, B10.BR and B10.P strains were immunized with 4 ug of HBcAg and draining lymph node cells were harvested 8 days post-immunization and cultured in vitro with the synthetic peptide or particulate HBcAg as the positive control. T cell activation was measured by IL-2 production as described in Example 5 using various polypeptide concentrations ranging from about 0.00003 to about 64 ug/ml.

The IL-2 production elicited by the optimal concentration of each peptide is shown in FIG. 9, that concentration ranging from about 16–64 ug/ml. The particulate HBcAg concentration was 0.5 ug/ml.

FIG. 9 indicates that distinct peptides were recognized by the differing murine strains. The C3H.Q strain recognized the p1-20 and the p100-120 sequences. The B10.S strain recognized the p28-52 and the p120-140 sequences. The B10.D2 stain recognized the p70-94, p85-100 (overlapping) and p120-140 sequences. The B10 strain recognized the p120-140 sequence exclusively. The B10.M strain recognized the p100-120 sequence exclusively. T cell recognition sites for the B10.BR and B10.P strains have not yet been identified.

Most importantly, the above results indicate that all the T cell active sites are common to both the HBcAg and HBeAg amino acid residue sequences. This suggests these antigens are crossreactive at the T cell level in contrast to the situation at the B cell (antibody) level.

12. HBcAg T Cell Proliferation

The ability of synthetic peptide p120-140 to both induce and elicit an HBcAg-specific T cell proliferation response in the B10.S strain was examined. Groups of 4 mice were immunized in the hind footpads with either 4 ug of HBcAg or 100 ug of p120-140, and 8 days later draining lymph nodes were harvested and cultured with the indicated antigens in vitro, and IL-2 production was determined as described in Example 5.

FIG. 10, Panel A, illustrates that HBcAg-primed B10.S strain T cells recognized p120-140 very efficiently. Inspection of the dose response curve demonstrates that a p120-140 concentration as low as 0.00015 ug/ml was sufficient to elicit IL-2 production. B10.S strain, HBcAg-primed T cells did not recognize the p85-100 sequence. In the reciprocal study, B10.S mice were primed with p120-140. The p120-140-primed T cells recognized the immunizing peptide and not the p85-100 sequence, and recognized the native HBcAg (FIG. 10, Panel B). Note that the native protein primed peptide-specific T cell proliferation more efficiently than the peptide primed HBcAg-specific proliferation.

Figure 11B:
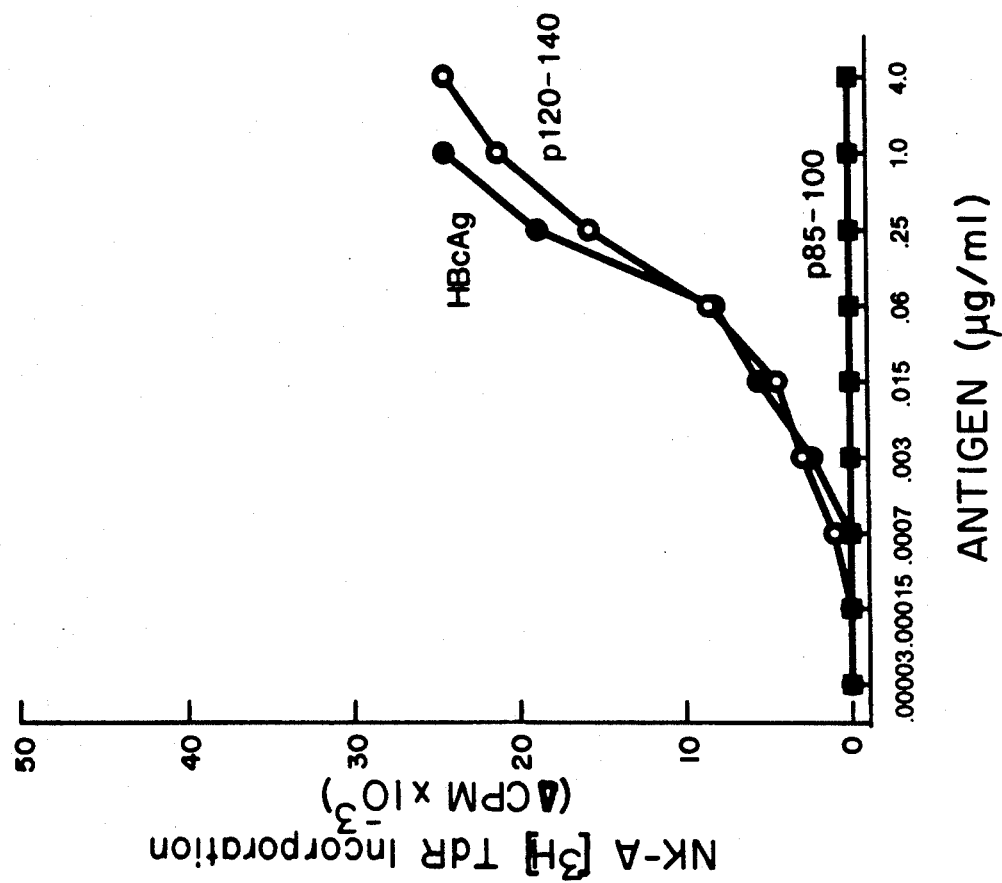
Figure 11A:
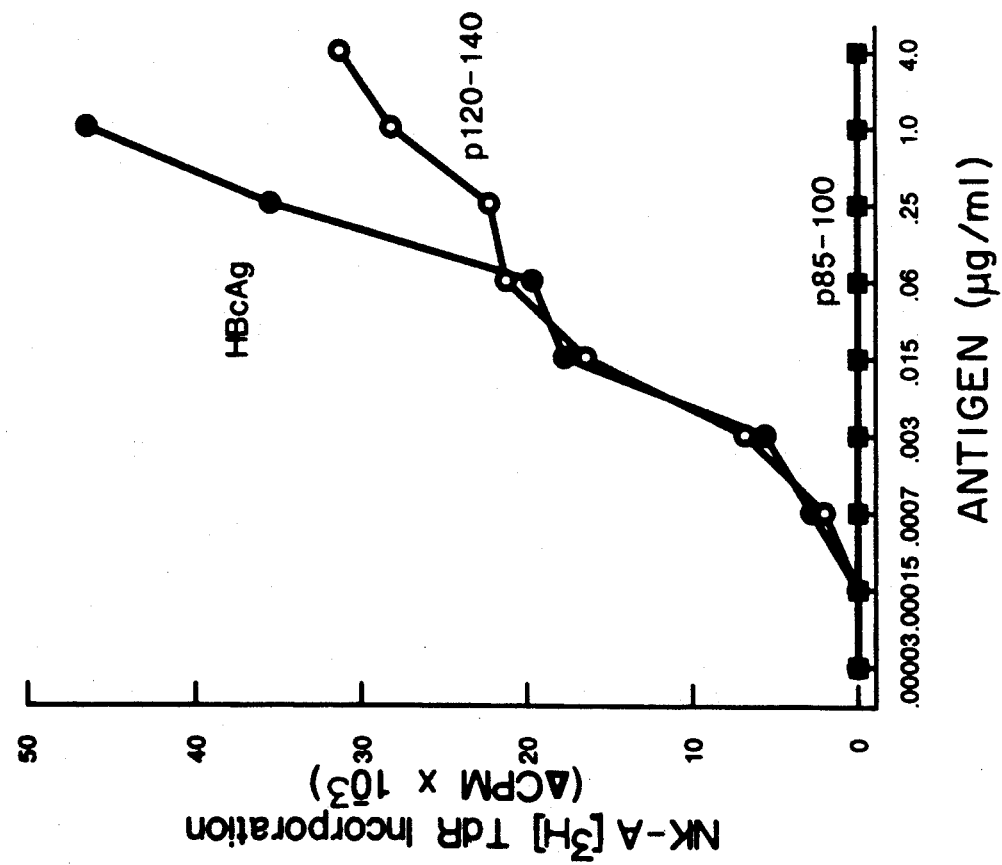

Similar studies were performed using the B10 mouse strain as a source of T cells. The results of those studies, shown in FIG. 11, indicate that in these studies the dose response curves for HBcAg and p120-140 appear to be even more closely related than in the B10.S strain. This may indicate that p120-140 represents the only T cell recognition site relevant for the B10 strain.

Figure 12A:
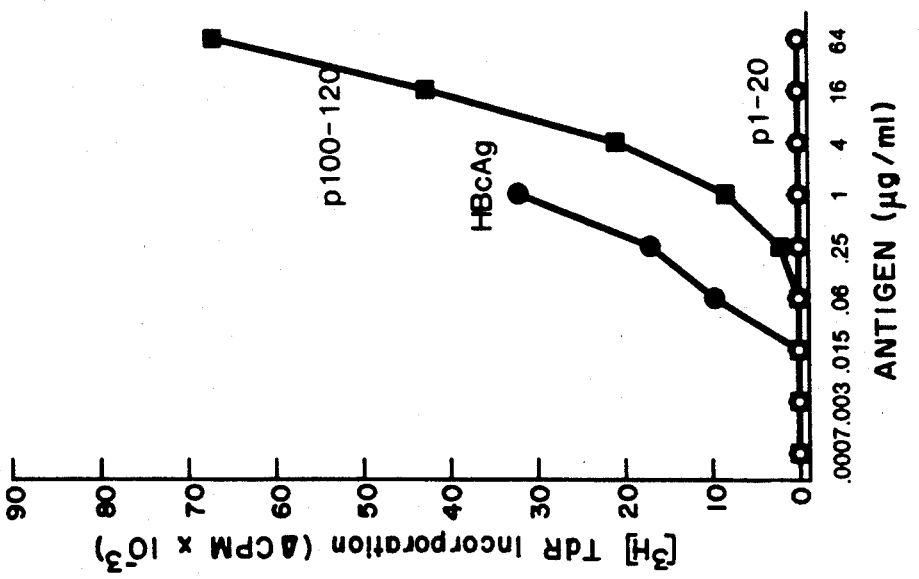
Figure 12B:
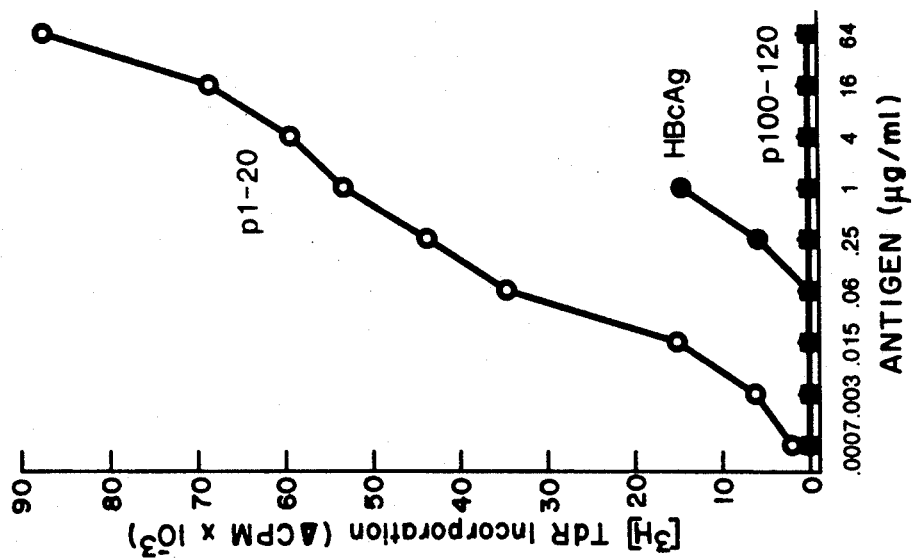
Figure 12C:
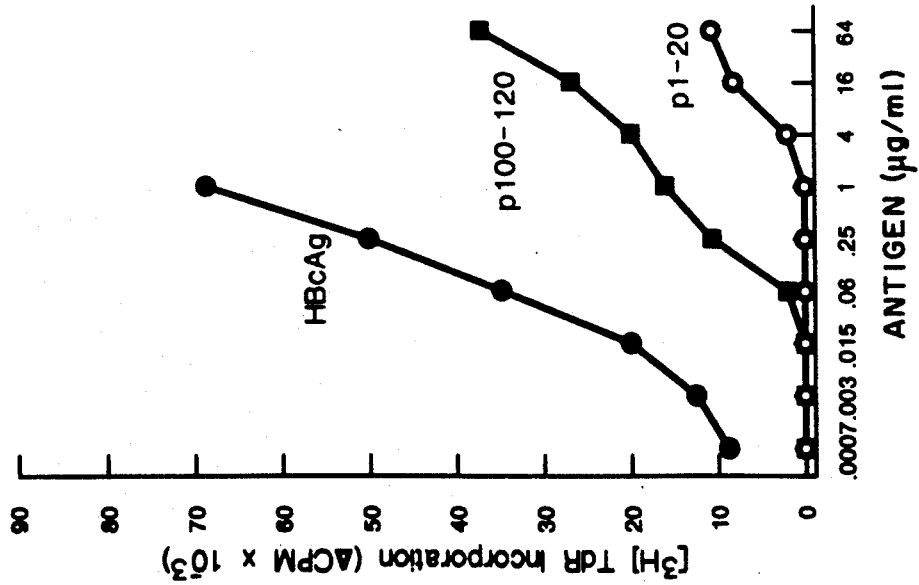

Similarly synthetic polypeptides p100-120 and p1-20 were examined for their ability to both induce and elicit a HBcAg-specific T cell proliferative response in the C3H.Q mouse strain. FIG. 12, Panel A, indicates that although HBcAg-primed C3H.Q T cells recognized both p100-120 and p1-20, p100-120 is a more efficient T cell stimulator. The ability of a peptide to induce a proliferative response does was not found to correlate with the ability of that peptide to induce a proliferative response relevant to the native protein. The p1-20 sequence is the superior peptide immunogen (FIG. 12, Panel B), however, p100-120 immunization elicits a better HBcAg-specific response (FIG. 12, Panel C).

Figure 13B:
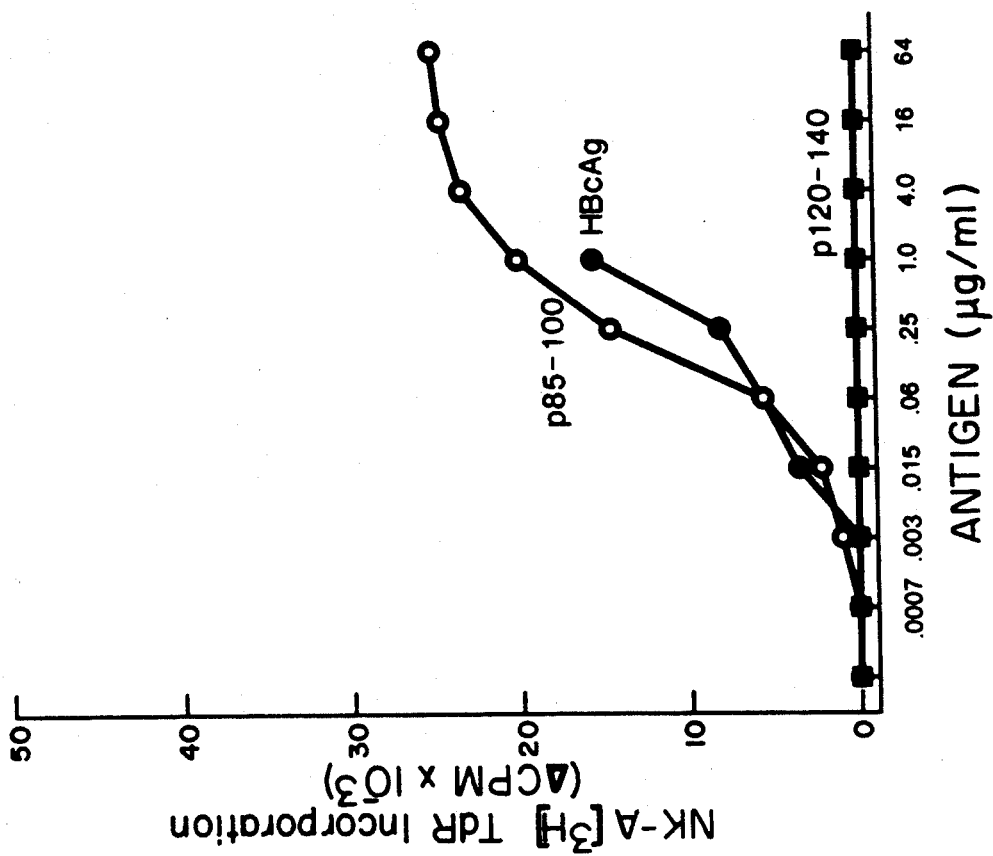
Figure 13A:
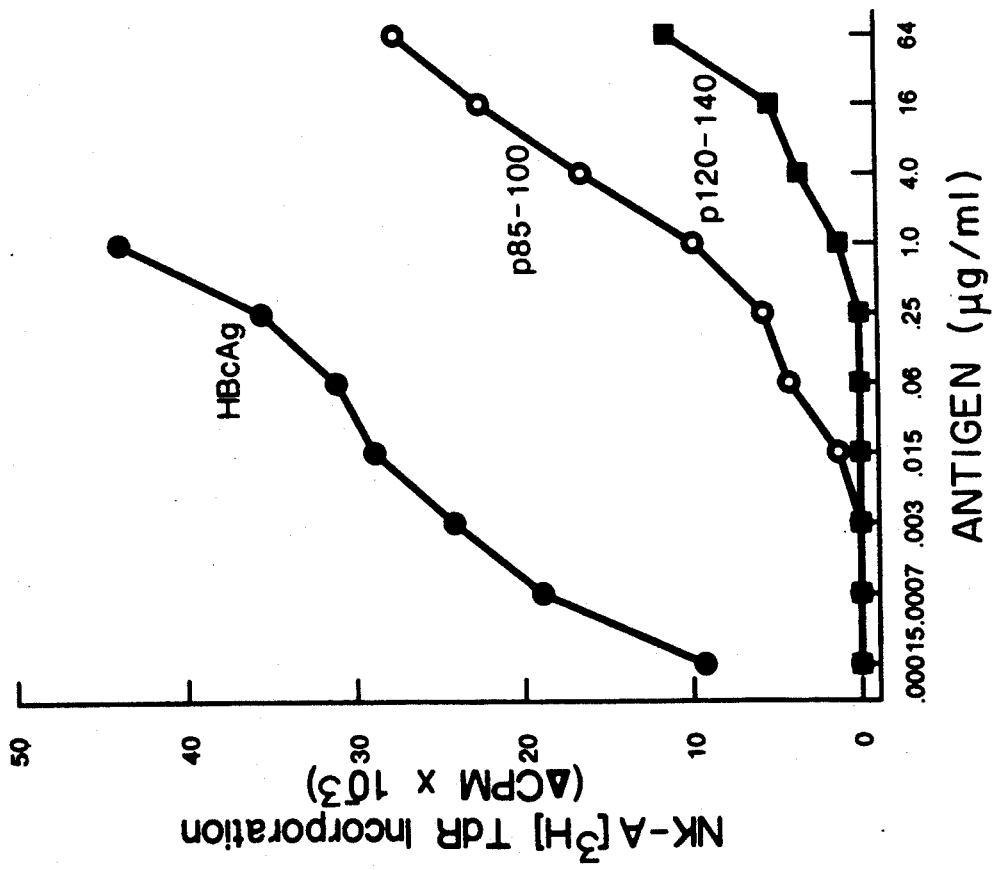

In a like manner, the ability of peptide p85-100 to both induce and elicit an HBcAg-specific T cell proliferative response in the B10.D2 strain was examined. As shown in FIG. 13, Panel A, strain B10.D2 particulate HBcAg-primed T cells were able to recognize both p85-100 and p120-140, although p85-100 is a more efficient T cell stimulator in this strain. Similarly, p85-100 was capable of priming T cells which recognized the native HBcAg and the immunizing peptide. (FIG. 13, Panel B).

13. Antibody Class and Subclass Distribution in an Anti-HBcAg Response

To determine if the production of IgG class, anti-HBcAg antibodies strictly required T cell influence, the class and IgG subclass distribution of anti-HBcAg production was investigated in B10.BR +/+ and B10.BR nu/nu mice immunized with HBcAg (Table 3).

TABLE 3

| Class and Subclass Distribution of Anti-HBcAg Antibodies Produced in B10.BR Euthymic (+/+) and B10.BR Athymic (nu/nu) Mice | | | | | | | |
|---|---|---|---|---|---|---|---|
| | | Anti-HBcAg Response | | | | | |
| Strain[1] | Days[2] | IgM | PolyIgG | $IgG_1$ | $IgG_{2a}$ | $IgG_{2b}$ | $IgG_3$ |
| B10.BR (+/+) | 10 | 2,560 | 40,950 | 40 | 2,560 | 10,240 | 640 |
| | 24 | 1,280 | 163,840 | 640 | 20,480 | 163,840 | 2,560 |
| B10.BR (nu/Nu) | 10 | 1,280 | 2,560 | 0 | 0 | 2,560 | 0 |
| | 24 | 1,280 | 2,560 | 0 | 40 | 2,560 | 0 |

[1]Groups of five euthymic (+/+) or athymic (nu/nu) B10.BR mice were immunized with 4.0 ug of HBcAg in CFA, and sera were analyzed by RIA, as described in Example 4, for antibodies to HBcAg of the IgM class and IgG class and subclasses (using IgG subclass-specific second antibodies) at days 10 and 24. Data are expressed as the reciprocal of the highest serum dilution to yield 4× the counts of preimmunization sera (titer).
[2]The number of days after immunization that sera were harvested.

Analysis of the data in Table 3 indicates that euthymic B10.BR mice produced anti-HBcAg of the IgM class and the entire spectrum of IgG subclasses at 10 and 24 days after immunization, although antibodies of the $IgG_{2b}$ subclass predominated. Note that IgM antibody declined slightly between day 10 and 24, whereas IgG antibodies showed a 4 to 16-fold increase. The B10.BR nu/nu mice also produced an IgG class, anti-HBcAg response of equivalent to higher titer than the IgM class response; however, the IgG response was exclusively of the $IgG_{2b}$ subclass. Therefore, production of anti- HBcAg of the IgG class per se is not a marker of T cell sensitization, but increased IgG subclass diversification and elevated IgG titers is. In these experiments a single, relatively small dose of particulate HBcAg was used, whereas the amount of HBcAg produced during HBV infection would be greater, and would persist throughout the viral replicative phase.

14. Ability of T Cell-Stimulating Polypeptide Primed T Cells to Help Produce Antibody to a Pathogen-Related Immunogen The ability of HBcAg primed T cells to function as T helper cells (Th) for antibody production to surface envelope (HBsAg) epitopes even though HBsAg and HBcAg are on distinct molecules within the same virion, was examined. Groups of five B10.S mice were primed by intraperitoneal immunization with either CFA alone, 4.0 ug of HBcAg in CFA, or 100 ug of the synthetic peptide p120-140 in CFA. Three weeks after priming, mice were challenged either with inccomplete adjuvant alone, or a suboptimal dose of a mixture of HBcAg (0.1 ug) and HBsAg/P39 (0.6 ug), or with HBV (0.4 ug) in incomplete adjuvant. The HBsAg/P39 and the HBV preparations were of the adw$_2$ subtype and were equilibrated to contain approximately equivalent amounts of S, pre-S(2) and pre-S(1) region antigenicity as described in Milich et al., *J. Immunol.*, 137:315 (1986). Seven days after the challenge dose, sera were collected, pooled, and analyzed for IgG antibody specific for the S, pre-S(2), and pre-S(1) regions of HBsAg by the solid-phase RIA described in Milich et al., *J. Immunol.*, 137:315 (1986). The solid-phase ligands used to detect anti-S, anti-pre-S(2), and anti-pre-S(1)-specific antibodies were: HBsAg/P25, a pre-S(2) region sequence represented by p133-145, and a pre-S(1) region sequence represented by p94-117, respectively. The antibody titers were expressed as the reciprocal of the log$_2$ of the highest serum dilution required to yield four times the counts of sera before immunization.

The results of this study are shown in FIG. 14 and indicate that unprimed mice produced no envelope-specific antibody. Similarly, mice primed with HBcAg and challenged with a mixture of HBcAg and HBsAg/P39 produced no anti-HBs. However, mice primed with HBcAg and subsequently challenged with virions (HBV) produced anti-S, anti-pre-S(2), and anti-pre-S(1)-specific antibodies. This result suggested that HBcAg-primed T cells could function to help anti-envelope antibody production, and the Th cell activity required that HBcAg and HBsAg be present within the same particle (virion), since the mixture was ineffective.

To confirm the T cell nature of the above result (HBcAg priming also elicited anti-HBc), the identical study was performed using the synthetic T cell stimulating polypeptide p120-140, as the priming antigen. This peptide induces HBcAg-specific T cells but not HBcAg-specific B cells (antibody). The results obtained were similar to those using native HBcAg as the priming antigen (FIG. 14). Mice primed with p120-140 and challenged with HBV produced anti-envelope antibodies, whereas, p120-140-primed mice challenged with the mixture did not. It should also be noted that the B10.S strain is nonresponsive to the S region of HBsAg, yet priming with a HBcAg-specific peptide circumvented nonresponse to HBsAg/P25 by providing an alternate Th cell recognition site on the HBV which B10.S strain T cells recognized.

These results unambiguously demonstrate that HBcAg-primed T cells are competent to help S region, pre-S(2) region, and pre-S(1) region-specific B cell clones produce antibody if HBcAg and HBsAg are present within the same particle, i.e., are operatively linked. Furthermore, these results substantiate that intermolecular/intrastructural Th cell function is not unique to the influenza system, and synthetic T cell epitopes (T cell stimulating polypeptides) can mediate this response. The HBcAg-primed T cells of Balb/c mice were also capable of eliciting envelope-specific antibody production, however, much less efficiently than B10.S strain, T cells. Therefore, the efficiency of intermolecular/intrastructural Th cell function can vary, and may be related to the distinct fine specificity of T cell recognition of HBcAg amongst H-2 haplotypes.

15. Fine Specificity of Antibody Production After Priming with p120-140

The diversity of fine specificities of anti-envelope antibodies produced under the influence of HBcAg and p120-140-primed Th cells was examined next. Priming and challenge experiments were performed as described in Example 14 with the exception that sera were collected 7 and 14 days after the challenge dose. The results of this study are shown in Table 4.

TABLE 4

Fine Specificity of Anti-Envelope Antibody Production After Priming with HBcAg or p120–140 in B10.S Mice

| | | | Antibody Titer (1/dilution) | | | | | | |
|---|---|---|---|---|---|---|---|---|---|
| | | Time | S Region | | Pre-S(2) Region[3] | | Pre-S(1) Region[4] | | |
| Prime[1] | Challenge | (d) | Subtype[2] | group | p133-140 | p135-145 | p32-53 | p94-105 | p106-117 |
| 0 | HBV | 7 | 0 | 0 | 0 | 0 | 0 | 0 | 0 |
| | | 14 | 0 | 0 | 0 | 0 | 0 | 0 | |
| HBcAg | HBV | 7 | 640 | 0 | 80 | 40 | 160 | 80 | 320 |
| | | 14 | 2560 | 160 | 320 | 640 | 1280 | 2560 | 1280 |
| p120-140 | HBV | 7 | 80 | 0 | 160 | 80 | 160 | 0 | 160 |
| | | 14 | 320 | 40 | 1280 | 160 | 320 | 320 | 160 |

[1]Groups of 4 B10.S mice were primed with CFA alone (0), 4.0 ug of HBcAg in CFA, or 100 ug of p120–140 in CFA. Three weeks later, all mice were challenged with a suboptimal dose of HBV (0.4 ug) in incomplete adjuvant, and sera were tested by RIA, as described in Example 14, for IgG antibody against the panel of antigens 7 and 14 days after the challenge. Titers are expressed as the reciprocal of the serum dilution which yielded 4× the counts of preimmunization sera.
[2]HBsAg/P25 of the ad subtype was the solid-phase ligand used to detect subtype plus group-specific anti-S, whereas, HBsAg/P25 of the ay subtype was the solid-phase ligand used to detect group-specific anti-S.
[3]The pre-S(2) region synthetic peptides used have been previously shown to represent the dominant antibody binding sites within the pre-S(2) region.
[4]The pre-S(1) region synthetic peptides used have been previously shown to represent the dominant antibody binding sites within the pre-S(1) region. Milich et al., J. Immunol., 137:2703 (1986).

As shown in Table 4, priming with HBcAg or the synthetic T cell stimulating peptide p120-140 resulted in antibody production to seven distinct epitopes within the S and pre-S regions of HBsAg after challenge with HBV. Therefore, HBcAg-primed T cells are competent to provide functional T cell help to multiple B cell clones specific for a variety of antigenic determinants of the envelope, including 3 pre-S(1) epitopes, 2 pre-S(2) epitopes and group and subtype-specific epitopes of the S region. This is especially noteworthy in the context of p120-140-primed T cells, which represent a T cell population of relatively limited heterogeneity (i.e., one to several T cell specificities).

Figure 15:
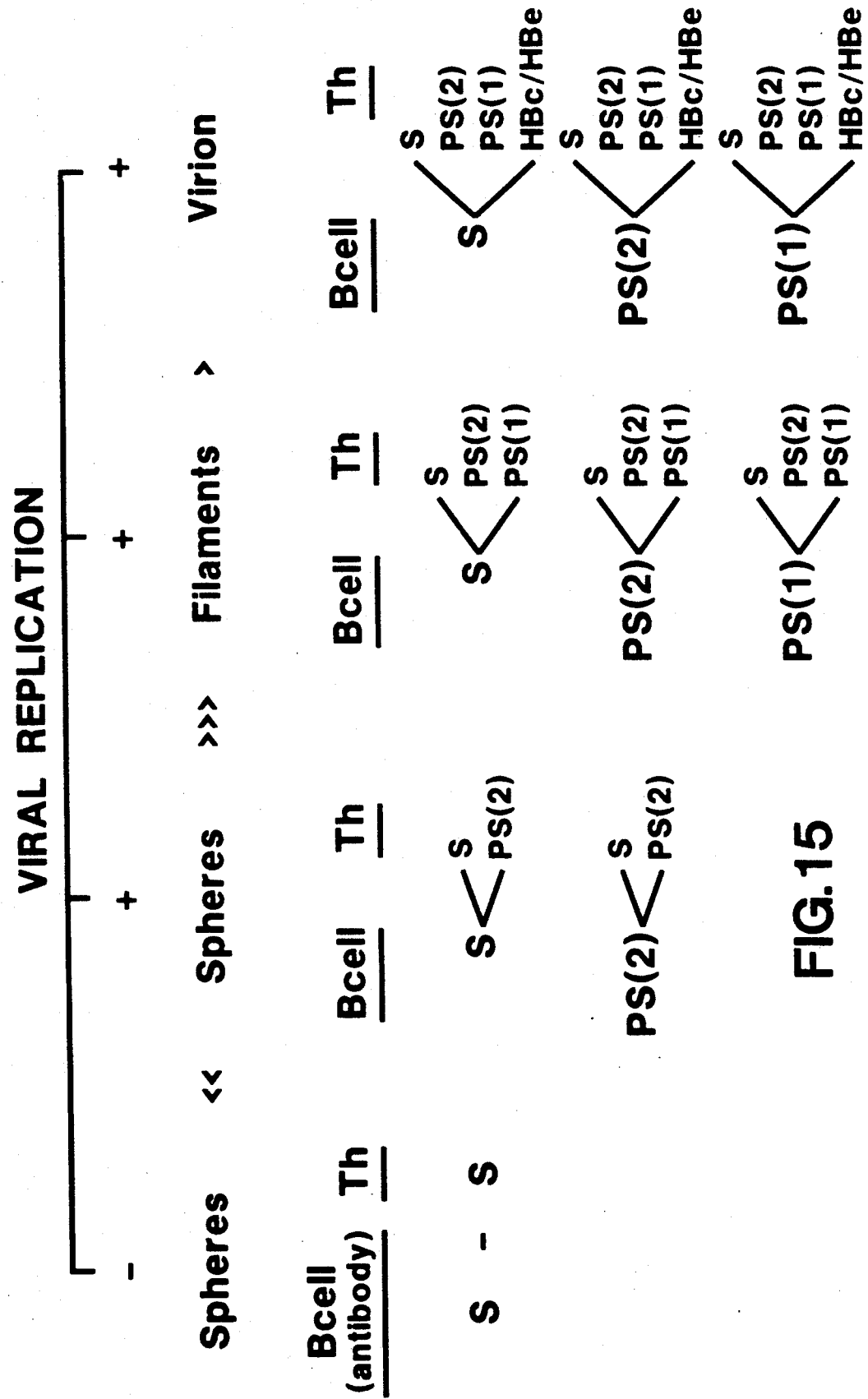

Regulation of the immune responses to pre-S and S region determinants of HBsAg has been extensively studied. Antibody production to the S, pre-S(2), and pre-S(1) regions of HBsAg are independently regulated by virtue of Th cells which recognize unique determinants on each region, and which are independently H-2 restricted. Furthermore, since S and pre-S region determinants exist on the same polypeptide (P39), Th cells specific for a determinant on one region are capable of providing functional help to B cell clones recognizing a determinant on another region. See FIG. 15. Therefore, S region and pre-S(2) region nonresponsiveness can be circumvented by immunization with HBsAg/P39.

Cumulatively, these observations suggest that after vaccination with HBsAg/P39 or during infection with HBV, all or none of the anti-envelope specificities should be produced. In general, the clinical observations to date support this prediction. Production of antibodies specific for the S, and pre-S regions occurs during resolving acute HBV infection, but not during the acute phase or subsequently in chronic HBV infection. However, a subset of chronically infected HBV patients has been reported to produce only anti-pre-S(1) in the absence of anti-pre-S(2) or anti-S antibodies, which correlated with seroconversion from HBeAg to anti-HBe status and viral clearance. Similarly, a proportion of animals chronically infected with the ground squirrel hepatitis virus were reported to produce only anti-pre-S(1) envelope antibody. These observations cannot be explained solely by the existing data, and emphasize that additional factors may influence antibody production during natural infection as opposed to vaccination.

The data presented herein suggest that progression to chronic infection requires, or is a consequence of nonresponsiveness to the envelope antigens at the T cell level, and furthermore, that anti-pre-S(1) production in the absence of anti-pre-S(2) and anti-S production is mediated by Th cells specific for HBcAg/HBeAg determinants. This is consistent with the correlation of anti-pre-S(1) production with anti-HBe seroconversion, and the ability of HBcAg/HBeAg-specific T cells to help envelope-specific antibody production as described herein. The question then arises as to why only anti-pre-S(1) is produced, since HBcAg-specific Th cells can also function to help anti-S and anti-pre-S(2) antibody production. This may be explained by the fact that subviral, 22 nm spherical particles lacking nucleocapsid antigens (HBcAg) circulate at levels in great excess of intact virions during HBV infection. The spherical particles express both S and pre-S-(2) region antigens but no or only minimal pre-S-(1) region antigens. See FIG. 15. Therefore, B cells specific for S and pre-S(2) region determinants are far more likely to bind spherical particles than virus, and will not benefit from HBcAg-specific Th cells. In contrast, pre-S(1)-specific B cells are more likely to recognize their ligand or intact virions because P39 is preferentially associated with the virus. Filamentous subviral particles also contain P39, however, this morphologic form is less prevalent in serum as compared to the spherical particles. See FIG. 15.

The fact that HBV chronic infection, in the context of nonresponse to the envelope antigens, frequently resolves with time suggests that viral clearance is a complex process, and the requirement for a Th cell response to envelope antigens may be circumvented. Conceivably, only anti-pre-S antibody production is required to neutralize viral infectivity from cell to cell, and HBcAg/HBeAg-specific Th cell function can substitute for pre-S-specific Th cells in this regard. Concurrently, a cytotoxic T lymphocyte (CTL) response specific for HBcAg/HBeAg may be required to eliminate cells replicating virus, as has been suggested by others. Whether CTL distinguish between HBcAg and HBeAg, as B cells do, or recognize HBcAg and HBeAg in a crossreactive fashion, as Th cells do, remains to be determined.

The fact that HBcAg/HBeAg-specific Th cells can elicit anti-envelope antibodies, which are virus neutralizing may explain the reported ability of HBcAg vaccination to protect against HBV infection. Furthermore, since HBcAg/HBeAg-specific Th cells were shown herein to induce anti-S antibody production in S region nonresponder mice, the present studies describe another mechanism of circumventing HBsAg nonresponsiveness. The only requirement is that HBcAg and HBsAg be operatively linked so as to be capable of inducing intermolecular/intrastructural Th cell function.

16. Fine Specificity of T Cell Recognition of the HBcAg-Specific Peptide p120-140 is Dependent on the H-2 Haplotype of the Responding Strain It has been demonstrated that HBcAg-primed T cells of $H-2^s$ and $H-2^b$ strain mice predominantly recognized the p120-140 sequence of HBcAg. It was, therefore, of interest to determine if each haplotype recognized the same or distinct sites within the p120-140 sequence. For this purpose, N-terminal (p120-131), C-terminal (p129-140), and an overlapping peptide (p125-136) were synthesized. Groups of 4 B10.S, B10 or B10.BR mice were primed in the hind footpads with either 4.0 ug of HBcAg or 100 ug of the synthetic peptides: p120-140, p120-131, or p129-140 in CFA. Eight days after priming, draining PLN cells were harvested, pooled and cultured with varying concentrations (0.00015-16 ug/ml) of HBcAg, p120-140, p120-131, p129-140, p125-135 or media alone, and T cell sensitization was measured by T cell proliferation (Tp) as described in Example 7. As illustrated in FIG. 16a, B10.S ($H-2^s$), HBcAg-primed T cells proliferated in response to HBcAg, the large peptide p120-140 and the N-terminal peptide p120-131, but not to the C-terminal peptide p129-140. Peptide p125-136 was also active, but significantly less than p120-131 (data not shown). It should be noted that the dose response curves for HBcAg-primed T cells stimulated with HBcAg or the active peptides were similar.

The reciprocal experiments involved priming with peptides and challenging in vitro with HBcAg or peptides. B10.S, p120-140-primed T cells recognized HBcAg, the immunizing peptide p120-140, and the N-terminal peptide p120-131, but not p129-140 (FIG. 16b). Therefore, similar to T cells primed with native HBcAg, p120-140-primed T cells recognized the N-terminal p120-131. Similarly, p120-131-primed T cells were activated by p120-140, p120-131 and HBcAg (FIG. 16c). Therefore, the 12 residue peptide, p120-131 was sufficiently immunogenic to prime HBcAg-specific T cells in vivo. Although peptide-primed T cells responded to HBcAg and the p120-131 sequence within the synthetic peptides, the responses to the synthetic peptides were more efficient, and this was especially true with respect to p120-131-primed T cells (FIG. 16 b, c). This is in contrast to B10.S HBcAg-primed T cells, which responded to HBcAg and the active peptides equivalently (FIG. 16a). The C-terminal peptide p129-140 was only marginally immunogenic in the B10.S strain (FIG. 16d).

Similar experiments were performed in H-2 cogenic (H-2$^b$) mice (FIG. 17). B10, HBcAg-primed T cells proliferated in response to HBcAg, p120-140, and the C-terminal fragment p129-140, but not to p120-131 or p125-136 in contrast to B10.S, HBcAg-primed T cells (FIG. 17a). Because the p120-140 sequence is common to both HBcAg and HBeAg, these results predict that HBcAg and HBeAg are crossreactive at the level of T cell proliferation. The use of recombinant HBeAg provided by Biogen SA, Geneva, Switzerland, allowed confirmation of this prediction because B10, HBcAg-primed T cells recognized HBeAg (FIG. 17a). B10, p120-140 or p129-140-primed T cells were specific for the C-terminal fragment p129-140, and recognized HBcAg approximately as well as the immunizing peptide (FIG. 17 B,D). Peptide p129-140-primed T cells also proliferated in response to HBeAg (FIG. 17d). The N-terminal fragment p120-131 was nonimmunogenic in the B10 strain (FIG. 17c). Identical experiments performed in B10.BR (H-2$^k$) mice revealed that although B10.BR, HBcAg-primed T cells recognized HBcAg and HBeAg, the p120-140 sequence and the truncated peptides were neither stimulatory nor immunogenic (data not shown).

17. Synthetic Peptides p120-140, p120-131, and p129-140 Can Prime Functional T Helper Cell Activity in Vivo As an alternative method of examining the fine specificity of T cell recognition of HBcAg and as a means of determining the functional ability of synthetic T cell stimulating polypeptides to prime antibody production in vivo, T helper cell assays were performed. T helper cell activity was determined by priming groups of four B10.S, B10, or B10.BR mice with 100 ug of the HBcAg-specific peptides, p120-140, p120-131, or p129-140 in CFA and challenging 21 days later with a suboptimal dose of HBcAg (0.1 ug) in incomplete adjuvant. Seven days after the challenge, serum anti-HBc antibody was measured by solid-phase RIA as described in Milich et al., *J. Immunol.*, 129:320-325 (1982).

Briefly, pooled murine sera were evaluated for antibody in an indirect, solid-phase radioimmunoassay (RIA) using solid-phase HBcAg (0.1 ug/well), HBsAg/GP33 (0.1 ug/well), or synthetic peptides (1 to 2 ug/well) and goat anti-mouse IgG as second antibody and were developed with an $^{125}$I-labeled, affinity-purified swine anti-goat Ig. Recombinant HBsAg particles containing approximately 35% GP33 were provided by P. Tiollais (Pasteur Institute, Paris, France), and are designated herein as HBsAg/GP33. The results were expressed as antibody titer representing the highest dilution to yield four times the counts of preimmunization sera.

Figure 18A:
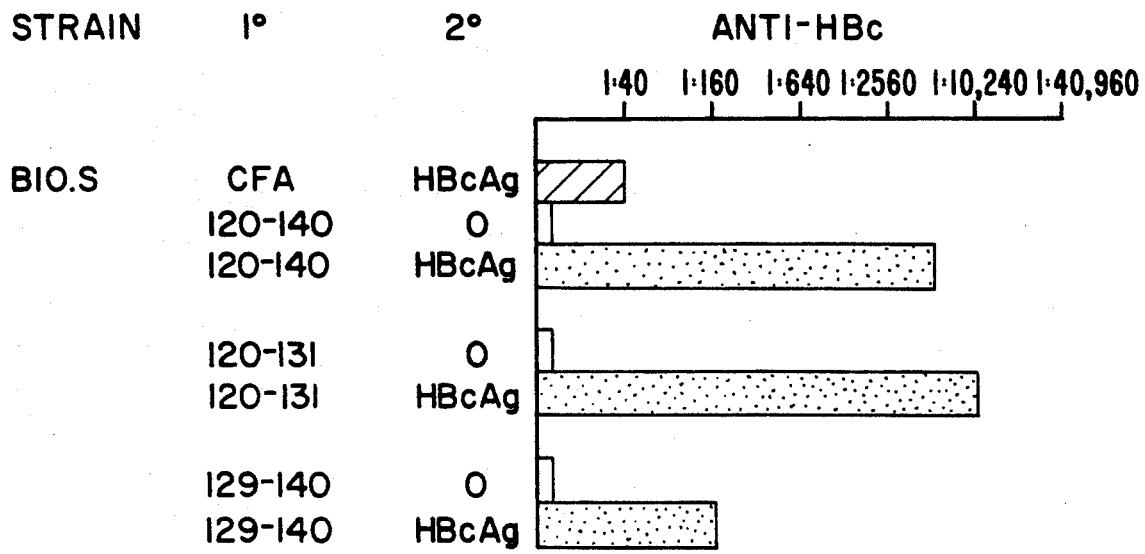

The controls consisted of priming mice with CFA alone and challenging with HBcAg, or peptide priming without HBcAg challenge. As shown in FIG. 18, priming with synthetic T cell sites, p120-140, p120-131, and p129-140 did not elicit anti-HBc antibody production in B10.S mice, and p129-140 induced only minimal anti-HBc in B10 mice. Therefore, although these peptides contain T cell recognition sites, the B cell epitopes present on the peptides are not relevant to or are not exposed on the active HBcAg, i.e., they are peptide-specific. Therefore, it was possible to examine the ability of these peptides to prime Th cells in vivo directly as opposed to performing T cell transfer experiments. This approach requires that the memory Th cells primed by immunization with peptide be recalled by challenge with HBcAg, indicating the relevance of the synthetic T cell recognition site to the native molecule.

Figure 18B:
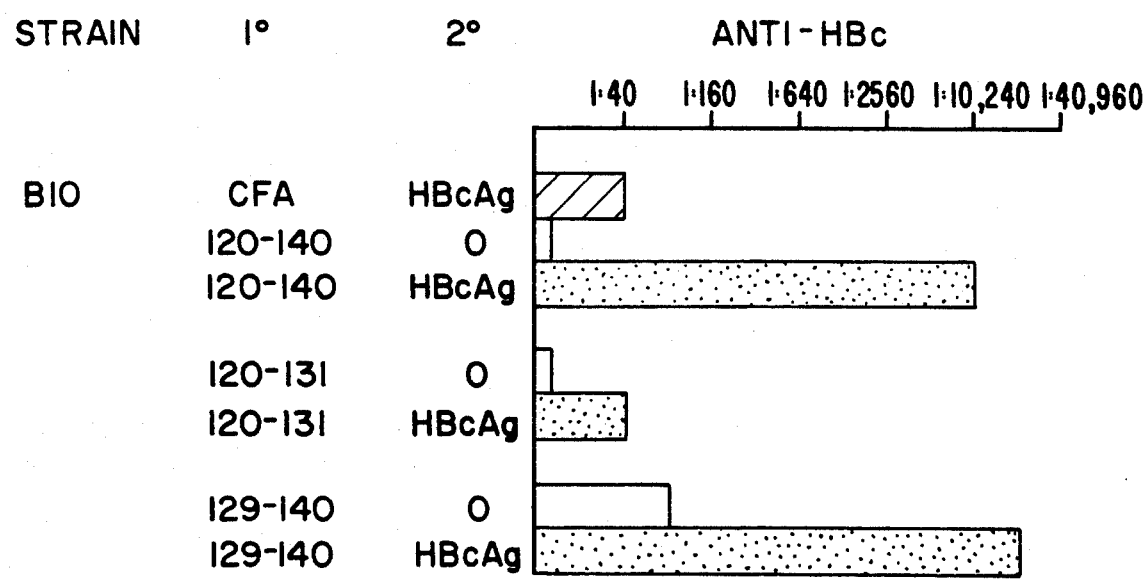

In the B10.S strain, unprimed mice challenged with HBcAg produced minimal anti-HBc (1:40) in vivo, whereas, p120-140-primed mice challenged with HBcAg produced IgG, anti-HBc efficiently (1:5120) 7 days after the challenge (FIG. 18, upper panel). To examine the fine specificity of the Th cell activity, B10.S mice were primed with the N- and C-terminal peptides and then challenged with HBcAg. Priming with the N-terminal peptide, p120-131, elicited significant anti-HBc production (256-fold unprimed) and the C-terminal peptide was only marginally reactive (4-fold unprimed) (FIG. 18). Similarly, immunization with p120-140 primed anti HBc production in the B10 strain (1:10,240). However, in contrast to the B10.S strain, the C-terminal peptide, p129-140, primed anti-HBc production in the B10 strain, and the N-terminal peptide was inactive (FIG. 18B, lower panel). The p120-140 sequence of HBcAg did not prime anti-HBc production in B10.BR mice (data not shown). These results are consistent with the T cell proliferation results and indicate a concordance between Tp and Th cell fine specificities.

18. The HBcAg-specific Peptide p120-140 Can Function as a T Cell Carrier Moiety for a Synthetic B Cell Epitope From the Envelope of HBV Because the p120-140 sequence was shown to encompass distinct Th cell recognition sites for B10.S and B10 mice capable of inducing anti-HBc production in vivo, peptide p120-140 was coupled directly to a synthetic B cell epitope and its ability to act as a T cell carrier for that epitope was examined. The B cell epitope chosen was the pre-S(2) region peptide p133-140 (DPRVRGLY), which was previously shown to represent a dominant antibody binding site within the pre-S(2) region of HBsAg/GP33 particles. The unconjugated p133-140 sequence of the pre-S(2) region is nonimmunogenic in the B10.S, B10 and B10.BR strains (data not shown). Groups of 5 B10.S, B10 and B10.BR mice were immunized with 100 ug in CFA of a composite peptide composed of residues 120-140 from the HBcAg sequence and residues 133-140 from the pre-S(2) region of the envelope, the composite polypeptide immunogen being designated c120-140-(133-140). Mice were boosted with 50 ug of the composite peptide in incomplete adjuvant 4 weeks later. Sera were collected preimmunization, 3 weeks after the primary immunization (1°), and 2 weeks after the secondary immunization (2°) and analysed for IgG class, antibodies specific for the T cell carrier peptide, c120-140, HBcAg particles, the B cell epitope (133-140), and HBsAg/GP33 envelope particles by solid-phase RIA as described in Example 17. The results of this study are shown in Table 5 antigen is depicted in FIG. 19. B10.S, c120-140-(133-140)-primed T cells responded to c120-140, the N-termi-

TABLE 5

The HBcAg-Specific p120-140 Sequence Can Function as a T Cell Carrier for a Synthetic Pre-S(2) Region B Cell Epitope (133-140)

| Strain | Immunogen[1] | Time | Antibody Titer (1/Dilution)[2] | | | |
|---|---|---|---|---|---|---|
| | | | c120-140 | HBcAg | (133-140) | HBsAg/GP33 |
| B10.S | c120-140-(133-140) | Pre | 0 | 0 | 0 | 0 |
| | | 1° | 10,240 | 0 | 640 | 1,280 |
| | | 2° | 40,960 | 1,280 | 10,240 | 10,240 |
| B10 | c120-140-(133-140) | Pre | 0 | 0 | 0 | 0 |
| | | 1° | 1,280 | 0 | 0 | 0 |
| | | 2° | 81,920 | 5,120 | 2,560 | 1,280 |
| B10.BR | c120-140-(133-140) | Pre | 0 | 0 | 0 | 0 |
| | | 1° | 0 | 0 | 0 | 0 |
| | | 2° | 0 | 0 | 0 | 0 |

[1]The indicated strains were immunized i.p. with 100 ug of c120-140-(133-140) in CFA, and boosted 4 weeks later with 50 ug i.p. in incomplete adjuvant. Sera were collected preimmunization (Pre), 3 weeks after the primary immunization (1°), and 2 weeks after the secondary immunization (2°).
[2]Antibody (IgG) specific for the indicated antigens was measured by solid-phase RIA, and expressed as the reciprocal of the dilution to yield 4× the counts of preimmunization sera.

After primary immunization with c120-140-(133-140) the B10.S strain produced antibody to the HBcAg-specific peptide (c120-140), which did not crossreact with native HBcAg (i.e., peptide-specific); and antibody to the pre-S(2) region peptide (133-140), which did crossreact with native HBsAg/GP33 particles. After the secondary immunization all antibody titers increased from 4-fold (anti-c120-140) to 16-fold (anti-133-140). Note that the secondary anti-c120-140 antibody was only minimally reactive with the native HBcAg protein, whereas, the anti-(133-140) antibody was highly crossreactive with the native HBsAg/GP33 protein. The B10 strain was less responsive to c120-140-(133-140) immunization than the B10.S strain as evidenced by the necessity for a booster immunization to elicit anti-(133-140) antibody production, which was 4 to 8-fold less as compared to the secondary response of the B10.S strain (Table 5). Similar to the B10.S strain, the B10, anti-(133-140) antibody was highly crossreactive with native HBsAg/GP33, whereas, anti-c120-140 was only minimally crossreactive with native HBcAg. Both the B10.S and B10 strains produced high-titered, predominantly peptide-specific antibody to the c120-140 sequence. In both strains the antibody was specific for the C-terminal fragment, p129-140 (data not shown). Predictably from the T cell proliferation and Th cell experiments, the B10.BR strain was a nonresponder to immunization with c120-140-(133-140). These results indicate that the HBcAg-specific synthetic peptide p120-140 can function as a T cell carrier for a synthetic B cell epitope represented on the envelope of the HBV in strains which recognize the 120-140 sequence of HBcAg at the T cell level.

19. Fine Specificity of T Cell Recognition of the Synthetic Immunogen, c120-140-(133-140)

Figure 19A:
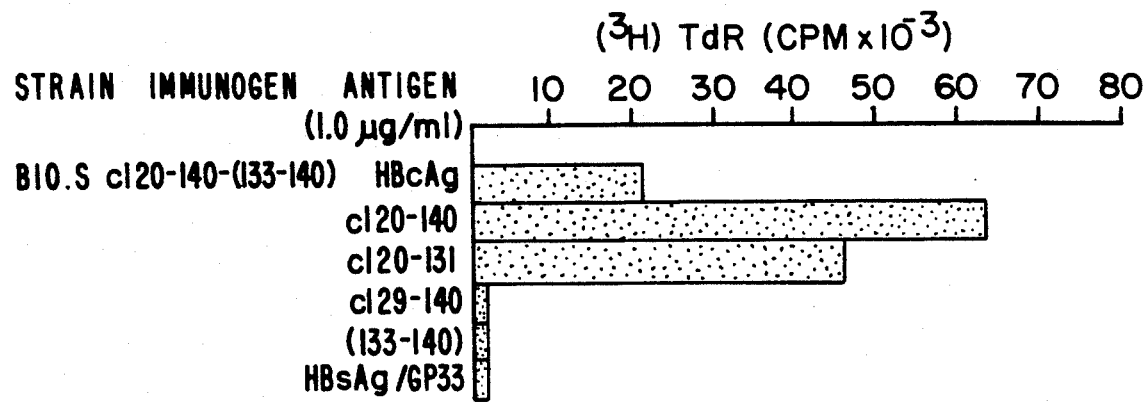
Figure 19B:
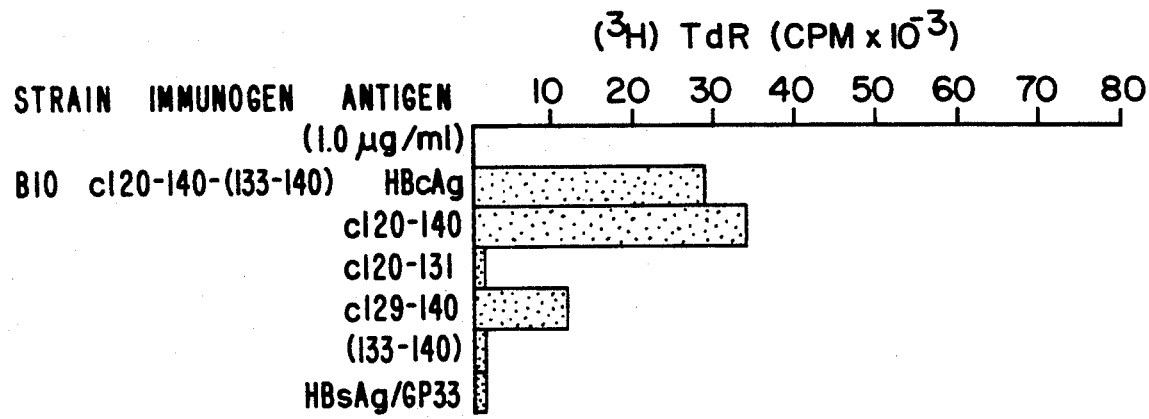
Figure 19C:
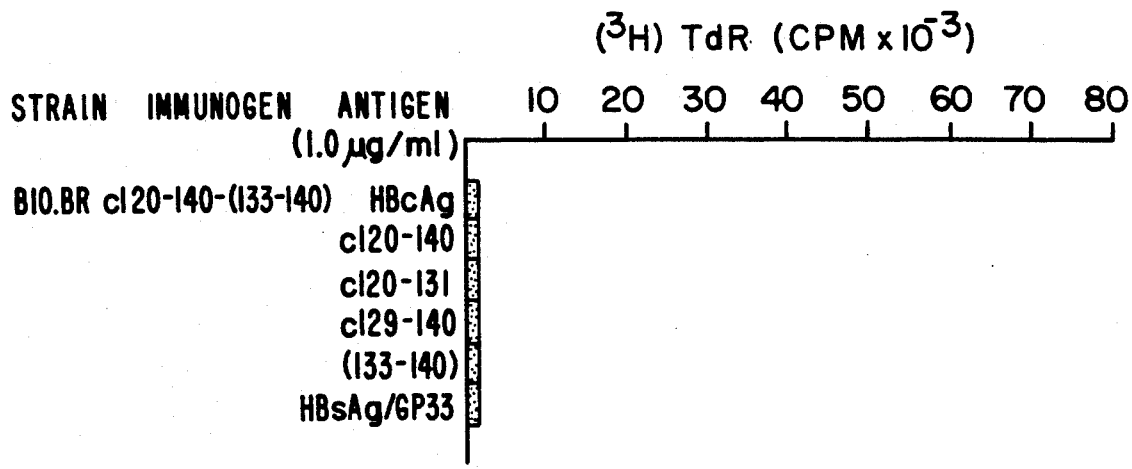

In order to confirm that the predicted sites within the composite immunogen were functioning as T cell recognition sites, c120-140-(133-140) immunized mice were evaluated at the T cell level. Groups of 4 B10.S, B10, and B10.BR mice were immunized with 100 ug of c120-140-(133-140) in CFA in the hind footpads, and the draining PLN cells were harvested 8 days later. Composite peptide-primed T cells were cultured with varying concentrations of HBcAg, HBsAg/GP33, the HBcAg-specific peptides: p120-140, p120-131, p129-140; and the pre-S(2) region peptide (133-140), and T cell proliferation was determined. The level of T cell proliferation induced by a 1.0 ug/ml concentration of nal fragment, p120-131, and to native HBcAg. The B cell epitope (133-140) and native HBsAg/GP33 particles were non-stimulatory at all concentrations (FIG. 19A, top panel). B10. c120-140-(133-140)-primed T cells were activated by c120-140, the C-terminal fragment, p129-140, and native HBcAg. The B cell epitope (133-140) and native HBsAg/GP33 were nonstimulatory at all concentrations (FIG. 19B, middle panel). The significantly higher peptide-specific T cell proliferative responses of the B10.S strain as compared to the B10 strain may explain the greater anti-pre-S(2) antibody production observed in the B10.S strain after c120-140-(133-140) immunization (Table 5). B10.BR, c120-140-(133-140)-primed T cells were nonresponsive to the entire antigen panel (FIG. 19C, bottom panel). These results and the antibody results depicted in Table 5 indicate that T cell recognition of the composite peptide is H-2-dependent, and correlates with the specificity patterns observed for free p120-140 in terms of Tp and Th activities.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. An immunogenic fusion protein comprising a polypeptide immunogen consisting essentially of about 10 to about 30 amino acid residues operatively linked by a peptide bond to an amino-terminal flanking sequence and a carboxy-terminal flanking sequence, said amino-terminal flanking sequence consisting essentially of about 10 to about 20 amino acid residues having an amino acid residue sequence corresponding in sequence to a portion of HBV core protein from about position 1 to about position 35 and said carboxy-terminal flanking sequence consisting essentially of about 120 to about 160 amino acid residues having an amino acid residue sequence corresponding in sequence to a portion of HBV core protein from bout position 10 to about position 183.

2. An immunogenic fusion protein comprising a polypeptide immunogen consisting essentially of about 10 to about 30 amino acid residues operatively linked by a peptide bond to an amino-terminal flanking sequence and a carboxy-terminal flanking sequence, said amino-terminal flanking sequence consisting essentially of about 70 to about 90 amino acid residues having an amino acid residue sequence corresponding in sequence to a portion of HBV core protein from about position 1 to about position 90 and said carboxy-terminal flanking sequence consisting essentially of about 65 to about 85 amino acid residues having an amino acid residue sequence corresponding in sequence to a portion of HBV core protein from about position 80 to about position 183.

3. A T cell stimulating polypeptide consisting essentially of about 15 to about 70 amino acid residues having a sequence corresponding in sequence to a portion of the amino acid residue sequence of HBV core protein from about position 70 to about position 140 from the amino terminus thereof.

4. A composite polypeptide immunogen comprising at least 20 amino acid residues that includes a T cell stimulating polypeptide consisting essentially of about 15 to about 70 amino acid residues having a sequence corresponding in sequence to a portion of the amino acid residue sequence of HBcAg from about position 70 to about position 140 from the amino acid terminus thereof operatively linked to a polypeptide immunogen.

5. A method of enhancing the immunogenicity of a polypeptide immunogen comprising operatively linking to said polypeptide immunogen a T cell stimulating polypeptide consisting essentially of about 15 to about 70 amino acid residues having a sequence corresponding in sequence to a portion of the amino acid residue sequence of HBcAg from about position 70 to about position 140 from the amino terminus thereof.

* * * * *

UNITED STATES PATENT AND TRADEMARK OFFICE
CERTIFICATE OF CORRECTION

PATENT NO. : 5,143,726
DATED : September 1, 1992
INVENTOR(S) : Thornton, et al.

It is certified that error appears in the above-identified patent and that said Letters Patent is hereby corrected as shown below:

In Column 1, line 4, insert:

-- This invention was made with government support under Grant No. AI 20720-09 awarded by the National Institutes of Health. The government has certain rights in the invention. --

Signed and Sealed this

Eighteenth Day of January, 1994

Attest:

BRUCE LEHMAN

Attesting Officer          Commissioner of Patents and Trademarks

UNITED STATES PATENT AND TRADEMARK OFFICE
CERTIFICATE OF CORRECTION

PATENT NO. : 5,143,726
DATED : November 20, 1989
INVENTOR(S) : Thornton et al.

It is certified that error appears in the above-identified patent and that said Letters Patent is hereby corrected as shown below:

Column 1,
Line 4, before the heading "Cross-Reference to Related Application", add the governmental support paragraph with the following paragraph:

-- This invention was made with government support under Contract Nos. AI 20720 and AI 00585, by the National Institutes of Health. The government has certain rights in this invention. --

Signed and Sealed this

Fifteenth Day of July, 2003

JAMES E. ROGAN
*Director of the United States Patent and Trademark Office*